US012734052B2

(12) United States Patent
Cindrich et al.

(10) Patent No.: US 12,734,052 B2
(45) Date of Patent: Sep. 15, 2026

(54) BIFURCATED VASCULAR STENT AND METHODS OF MANUFACTURE

(71) Applicant: Merit Medical Systems, Inc., South Jordan, UT (US)

(72) Inventors: Christopher Cindrich, Highland, UT (US); John Hall, Bountiful, UT (US); Wayne Mower, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 709 days.

(21) Appl. No.: 18/054,717

(22) Filed: Nov. 11, 2022

(65) Prior Publication Data

US 2023/0149189 A1 May 18, 2023

Related U.S. Application Data

(60) Provisional application No. 63/380,316, filed on Oct. 20, 2022, provisional application No. 63/263,987, filed on Nov. 12, 2021.

(51) Int. Cl.
*A61F 2/856* (2013.01)
*A61F 2/06* (2013.01)
(Continued)

(52) U.S. Cl.
CPC ................ *A61F 2/856* (2013.01); *A61F 2/07* (2013.01); *A61F 2/86* (2013.01);
(Continued)

(58) Field of Classification Search
CPC .... A61F 2/856; A61F 2/07; A61F 2/86; A61F 2002/061; A61F 2002/067; B29C 41/14; B29K 2995/0056; B29L 2031/7534
See application file for complete search history.

(56) References Cited

U.S. PATENT DOCUMENTS 837,291 A 12/1906 Elliott
3,029,819 A * 4/1962 Starks ...................... A61F 2/06 156/143

(Continued)

FOREIGN PATENT DOCUMENTS

CN 102470029 A 5/2012
CN 110038208 A 7/2019

(Continued)

OTHER PUBLICATIONS

International Search Report and Written Opinion dated Mar. 15, 2024 for PCT/US2023/079538.

(Continued)

*Primary Examiner* — Jeffrey M Wollschlager
(74) *Attorney, Agent, or Firm* — Dorsey & Whitney LLP

(57) ABSTRACT

Bifurcated endovascular prostheses used to treat diseased blood vessels, such as arteries, are disclosed. In some embodiments, the bifurcated endovascular prosthesis is configured to be implanted within the diseased blood vessels adjacent a diseased section. The bifurcated endovascular prosthesis includes a primary stent graft and a secondary stent graft. The primary stent graft includes a pocket or sleeve disposed within a bore. A proximal portion of the secondary stent graft is disposed within the pocket or sleeve. Blood flow through the bifurcated endovascular prosthesis is divided into two flows, a first flow through the primary stent graft and a second flow through the secondary stent graft.

19 Claims, 16 Drawing Sheets

(51) Int. Cl.
*A61F 2/07* (2013.01)
*A61F 2/86* (2013.01)
*B29C 41/14* (2006.01)
*B29L 31/00* (2006.01)

(52) U.S. Cl.
CPC ... *A61F 2002/061* (2013.01); *A61F 2002/067* (2013.01); *B29C 41/14* (2013.01); *B29K 2995/0056* (2013.01); *B29L 2031/7534* (2013.01)

(56) References Cited

U.S. PATENT DOCUMENTS 3,901,106 A 8/1975 Causey
5,676,697 A 10/1997 Mcdonald
5,713,917 A 2/1998 Leonhardt et al.
5,824,055 A 10/1998 Spiridigliozzi et al.
6,045,557 A 4/2000 White et al.
6,231,563 B1 5/2001 White et al.
6,325,826 B1 12/2001 Vardi et al.
6,645,242 B1 11/2003 Quinn
7,032,478 B2 4/2006 Hu
7,144,421 B2 12/2006 Carpenter et al.
7,316,655 B2 1/2008 Garibotto et al.
7,604,660 B2 10/2009 Borg et al.
7,938,043 B2 5/2011 Hu
7,998,186 B2 8/2011 Hartley
8,052,736 B2 11/2011 Doig et al.
8,257,431 B2 9/2012 Henderson et al.
8,273,115 B2 9/2012 Hamer et al.
8,394,136 B2 3/2013 Hartley et al.
8,474,120 B2 * 7/2013 Hagaman .................. A61F 2/07 29/458
8,545,549 B2 10/2013 Hartley et al.
8,672,993 B2 3/2014 Chuter et al.
8,763,498 B2 7/2014 Hsieh
8,795,349 B2 8/2014 Huser et al.
8,870,946 B1 10/2014 Quinn
9,101,456 B2 8/2015 Hartley et al.
9,149,382 B2 10/2015 Greenberg et al.
9,314,328 B2 4/2016 Dake et al.
9,539,083 B2 1/2017 Krimsky et al.
9,815,179 B2 11/2017 Anderson et al.
9,861,505 B2 1/2018 Khoury
10,201,413 B2 2/2019 Shalev et al.
10,201,414 B2 2/2019 Hartley et al.
10,232,494 B2 3/2019 Yang
2002/0049412 A1 4/2002 Gandras
2002/0077692 A1 6/2002 Besselink
2003/0130725 A1 7/2003 Depalma et al.
2004/0049204 A1 3/2004 Harari et al.
2004/0098084 A1 5/2004 Hartley et al.
2004/0230287 A1 11/2004 Hartley et al.
2005/0043784 A1 2/2005 Yampolsky et al.
2005/0145075 A1 7/2005 Lee et al.
2005/0149168 A1 7/2005 Gregorich
2005/0235783 A1 10/2005 Shen
2005/0247167 A1 11/2005 Chaconas et al.
2006/0149351 A1 7/2006 Smirthwaite et al.
2006/0212113 A1 9/2006 Shaolian et al.
2006/0247756 A1 11/2006 Richter
2007/0088323 A1 * 4/2007 Campbell ............. A61M 25/10 604/523
2007/0168020 A1 7/2007 Brucker et al.
2008/0009937 A1 1/2008 Kipperman
2008/0103587 A1 5/2008 Henderson et al.
2008/0109066 A1 5/2008 Quinn
2008/0114438 A1 5/2008 Hartley et al.
2009/0012597 A1 1/2009 Doig et al.
2009/0043377 A1 2/2009 Greenberg et al.
2009/0163880 A1 6/2009 Kipperman
2009/0259298 A1 10/2009 Mayberry et al.
2011/0087318 A1 * 4/2011 Daugherty ................ A61F 2/07 623/1.13
2011/0087319 A1 4/2011 Hagaman et al.
2011/0265613 A1 11/2011 Hu
2011/0288627 A1 11/2011 Hartley et al.
2011/0308360 A1 12/2011 Hu
2012/0010695 A1 1/2012 Kipperman
2012/0150273 A1 6/2012 Centola
2012/0290069 A1 11/2012 Ivancev et al.
2013/0046371 A1 2/2013 Greenberg et al.
2013/0184810 A1 7/2013 Hall et al.
2013/0228049 A1 9/2013 Shen
2013/0268059 A1 10/2013 Hagaman et al.
2013/0269488 A1 10/2013 Huang
2014/0020518 A1 1/2014 Huang
2014/0060259 A1 3/2014 Hu
2014/0371838 A1 12/2014 Buddery et al.
2015/0127089 A1 5/2015 Ducke et al.
2015/0135909 A1 5/2015 Chen
2015/0230916 A1 8/2015 Ivancev et al.
2015/0250579 A1 9/2015 Howard et al.
2016/0008959 A1 1/2016 Hu et al.
2016/0067848 A1 3/2016 Lee et al.
2016/0129563 A1 5/2016 Hu
2016/0324670 A1 11/2016 Yamaguchi
2016/0375561 A1 12/2016 Chen
2017/0072544 A1 3/2017 Wang
2017/0136207 A1 * 5/2017 Shiono .............. B29C 45/14336
2017/0281332 A1 10/2017 Lostetter
2017/0333236 A1 11/2017 Greenan
2018/0029202 A1 2/2018 Chou et al.
2018/0228592 A1 8/2018 Eaton et al.
2018/0303598 A1 10/2018 Szopinski et al.
2019/0099264 A1 4/2019 Kalfa et al.
2019/0151073 A1 5/2019 Hartley
2019/0159886 A1 5/2019 Lourenco
2019/0247179 A1 8/2019 Lostetter
2019/0314959 A1 10/2019 Chen
2019/0321203 A1 10/2019 Zayed et al.
2020/0214826 A1 7/2020 Hidari
2020/0375724 A1 12/2020 Perkins et al.
2020/0390573 A1 * 12/2020 Folan ....................... D04C 3/48
2021/0106444 A1 * 4/2021 Hall ........................ A61F 2/856
2023/0013983 A1 1/2023 Silveira et al.
2023/0045493 A1 2/2023 Reijnen
2023/0149149 A1 5/2023 Cindrich et al.
2024/0156585 A1 5/2024 Nielsen et al.
2024/0156622 A1 5/2024 Hall et al.
2024/0156626 A1 5/2024 Nielsen et al.
2024/0156627 A1 5/2024 Adams et al.
2024/0225865 A1 7/2024 Xiao et al.
2024/0277464 A1 8/2024 Cindrich et al.
2024/0277501 A1 8/2024 Cindrich et al.
2024/0277502 A1 8/2024 Cindrich et al.
2024/0315858 A1 9/2024 Adams et al.
2025/0000678 A1 1/2025 Adams et al.
2025/0268734 A1 8/2025 Hall et al.

FOREIGN PATENT DOCUMENTS

CN 113260336 A 8/2021
DE 10201414 A1 7/2003
EP 0783873 A3 1/1999
EP 2068761 B1 2/2019
JP 2003502080 A 1/2003
JP 2011528258 A 11/2011
KR 1020120092627 8/2012
WO 199800090 1/1998
WO 1998004212 2/1998
WO 0074598 A1 12/2000
WO 2001030433 5/2001
WO 2003065935 8/2003
WO 2010132836 A2 11/2010
WO 2013040663 3/2013
WO 2018018114 2/2018
WO 2020203083 A1 10/2020
WO 2021076614 A1 4/2021
WO 2021158234 A1 8/2021
WO 2022060994 A1 3/2022

(56) References Cited

FOREIGN PATENT DOCUMENTS

| | | |
|---|---|---|
| WO | 2022216374 A2 | 10/2022 |
| WO | 2023086955 A1 | 5/2023 |

OTHER PUBLICATIONS

International Search Report and Written Opinion dated Mar. 20, 2024 for PCT/US2023/079678.
International Search Report and Written Opinion dated Apr. 24, 2024 for PCT/US2023/079627.
International Search Report and Written Opinion dated Apr. 6, 2023 for PCT/US2022/079724.
International Search Report and Written Opinion dated Apr. 12, 2023 for PCT/US2022/079743.
European Search Report dated Aug. 22, 2025 for EP22893886.6.
International Search Report and Written Opinion dated Oct. 14, 2024 for PCT/US2024/035452.
International Search Report and Written Opinion dated Jun. 10, 2024 for PCT/US2024/015923.
International Search Report and Written Opinion dated Jun. 17, 2024 for PCT/US2024/015854.
International Search Report and Written Opinion dated Jun. 21, 2024 for PCT/US2024/016184.
International Search Report and Written Opinion dated Jul. 17, 2024 for PCT/US2024/020977.
Extended European Search Report dated Aug. 20, 2025 for EP22893878.3.
International Search Report and Written Opinion dated Feb. 4, 2021 for PCT/US2020/055562.
Extended European Search Report dated Oct. 9, 2023 for EP20876491.0.
Office Action dated Feb. 15, 2024 for U.S. Appl. No. 17/070,242.
Office Action dated Sep. 10, 2024 for U.S. Appl. No. 17/070,242.
Notice of Allowance dated Dec. 19, 2024 for U.S. Appl. No. 17/070,242.
Office Action dated Mar. 11, 2026 for U.S. Appl. No. 18/508,539.
Office Action dated Mar. 13, 2026 for U.S. Appl. No. 18/054,817.
Office Action dated Mar. 24, 2026 for U.S. Appl. No. 18/151,885.
De La Cruz, et al., "Thoracoabdominal Aortic Aneurysm Repair with a Branched Graft", #Ann Cardiothorac Surg, 1 (3), 2012-01-01 00:00:00.0, 381-393.
Office Action dated Apr. 6, 2026 for U.S. Appl. No. 18/441,812.
Office Action dated Apr. 24, 2026 for U.S. Appl. No. 18/443,833.
Office Action dated Apr. 30, 2026 for U.S. Appl. No. 18/612,628.
Office Action dated May 1, 2026 for U.S. Appl. No. 18/442,312.
Office Action dated Jul. 2, 2026 for U.S. Appl. No. 18/054,817.

* cited by examiner 110
125
141
134
111
123
120
140
130
112

110
130
111

110
130
111

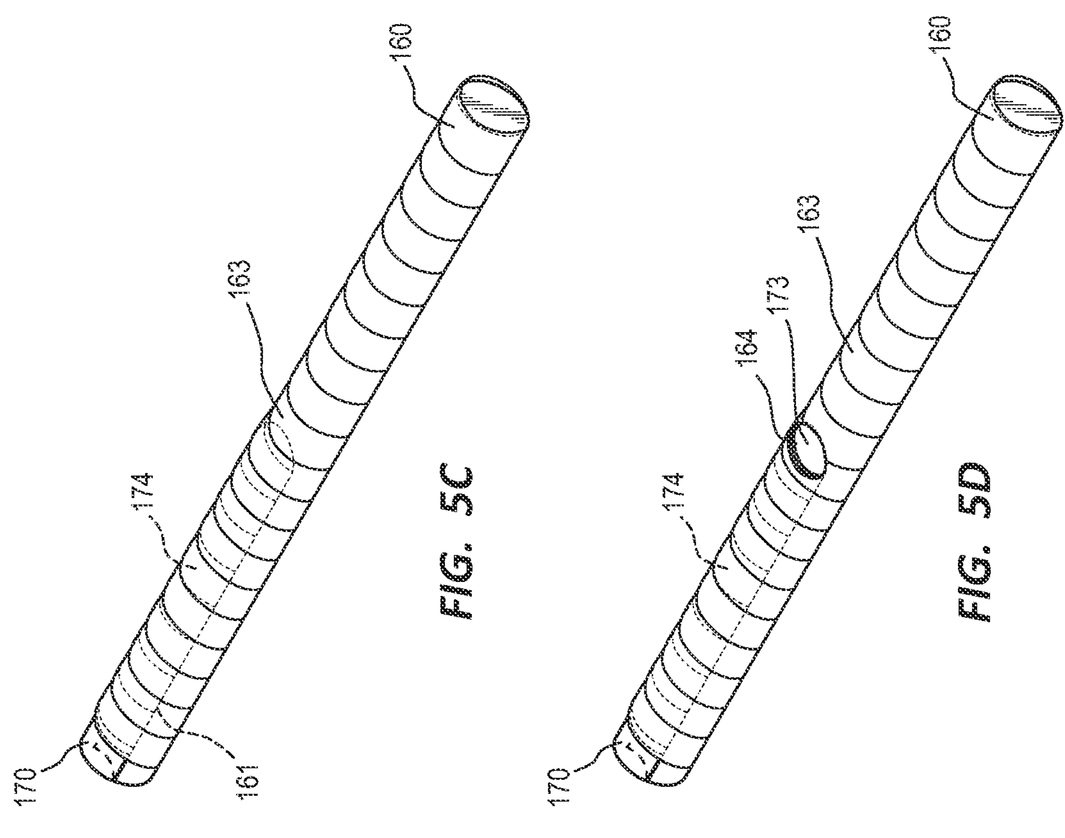
FIG. 5C
FIG. 5D
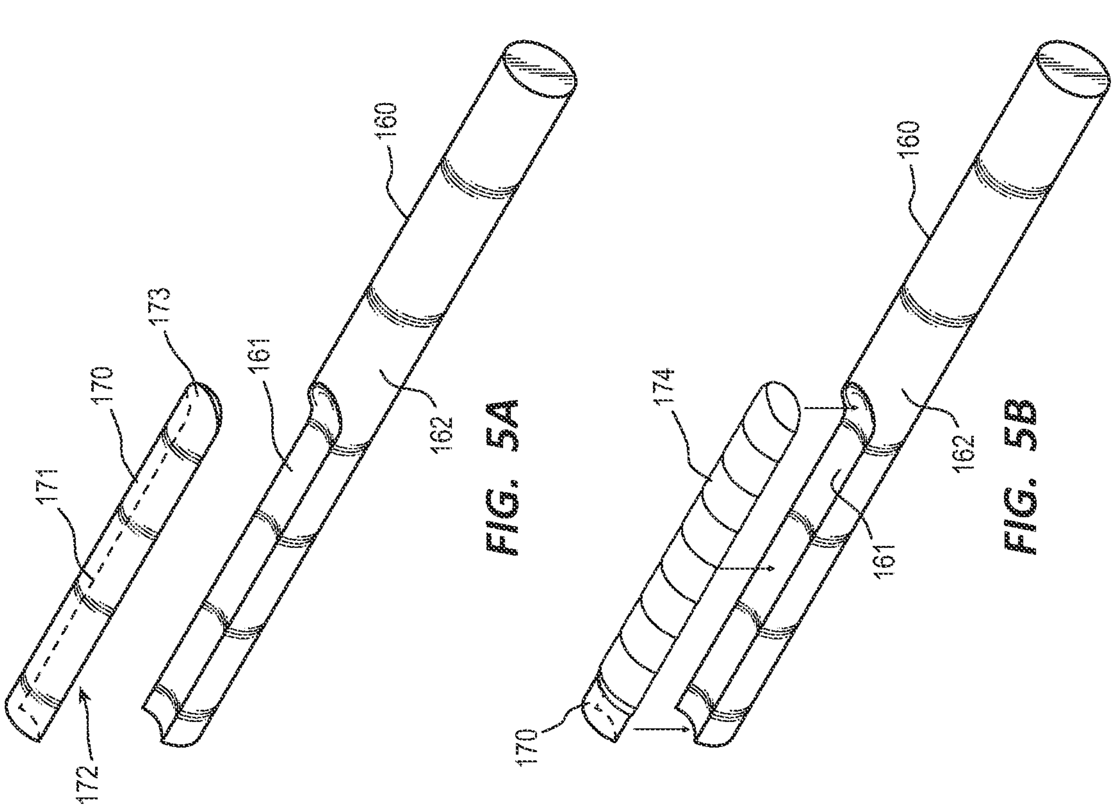
FIG. 5A
FIG. 5B

BIFURCATED VASCULAR STENT AND METHODS OF MANUFACTURE

RELATED APPLICATIONS

This application claims priority to U.S. Provisional Application No. 63/263,987, filed on Nov. 12, 2021 and titled, "Bifurcated Vascular Stent and Methods of Manufacture," and U.S. Provisional Application No. 63/380,316, filed on Oct. 20, 2022 and titled, "Bifurcated Vascular Stent and Methods of Manufacture," both of which are hereby incorporated by reference in their entireties.

TECHNICAL FIELD

The present disclosure relates to endovascular prostheses. In some embodiments, the present disclosure relates to bifurcated endovascular prostheses that may access to branch arteries when implanted in a major artery, such as the aorta. Methods of manufacture and use of prostheses are also disclosed.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 5A is a perspective view of an embodiment of a body mandrel and pocket mandrel.

FIG. 5B is a perspective view of the pocket mandrel of FIG. 5A covered with a polymeric covering.

FIG. 5C is a perspective view of the covered pocket mandrel of FIG. 5B coupled to the body mandrel of FIG. 5B and the body mandrel covered with a polymeric covering.

FIG. 5D is a perspective view of the covered body and pocket mandrels with an opening in the polymeric coverings.

DETAILED DESCRIPTION

Figure 1A:
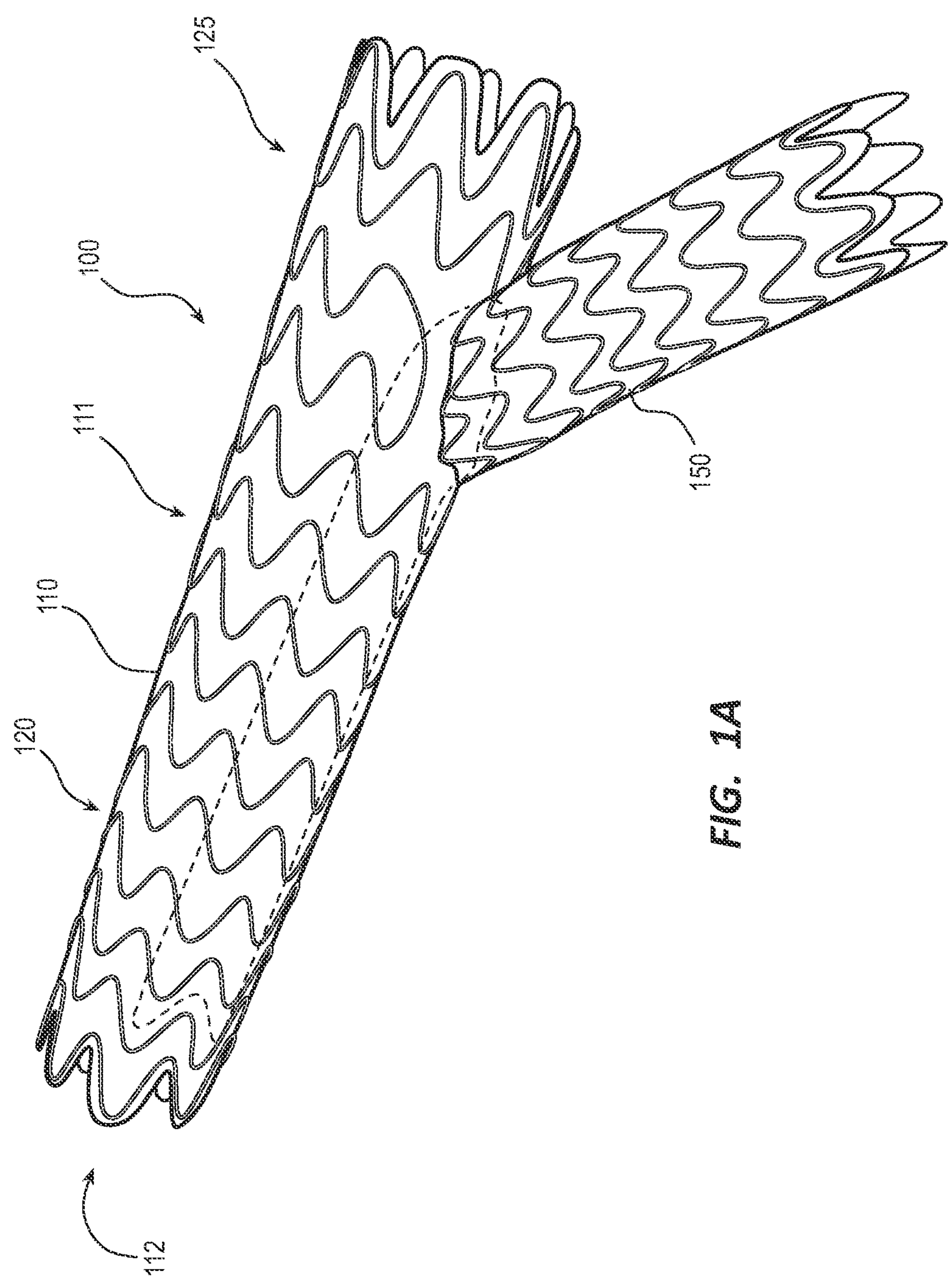
FIG. 1A is a perspective view of an embodiment of a bifurcated endovascular prosthesis.

Degenerative diseases of the vascular lumens of a human body, such as aneurysms and dissections, may be treated by vessel replacement, for example arterial replacement. Conventional open surgery for vessel replacement may be associated with significant risk of death or disability and may be especially dangerous for the vascular patient who typically has significant pre-existing surgical risk factors.

In some instances, diseased vascular lumens may be treated via minimally invasive alternatives to open vascular surgery, including processes whereby vessel replacement is performed by placement of an endovascular prosthesis via a remote access point. Such endovascular prostheses may be composed of an impervious fabric through which blood flows, preventing blood leakage though the prosthesis and directing blood flow through a portion of diseased vessel wall. The fabric may be sealed to a disease-free arterial wall above and below the diseased segment of vessel to be bypassed. Such endovascular prostheses may be utilized to repair disease of the arteries, including the thoracic and abdominal aortas as well as peripheral arteries and veins, such as the brachiocephalic veins. Tubular prostheses may be limited in their inability to repair branched vessels, as a sealed tubular construct positioned across the opening of a branch artery would prevent blood flow to the branch artery. Examples of regions of the aorta which may be affected by arterial disease that include branches include the aortic arch, from which the innominate, carotid, and subclavian arteries originate, and the proximal abdominal aorta, from which the visceral and renal arteries emerge as side branches.

Some embodiments of bifurcated endovascular prostheses within the scope of this disclosure may include a primary stent graft and a secondary stent graft. In some instances, bifurcated endovascular prostheses within the scope of this disclosure may be used to repair a section of the aorta adjacent the iliac arteries. In the examples that follow, and throughout this disclosure, discussion of treatment of one portion of the vasculature, such as the aorta, may be applicable to treat of other portions of the vasculature and/or other lumens of the human body, including portions of the vasculature or other lumens including a main lumen and intersecting branch lumens. For example, the bifurcated endovascular prostheses may be placed adjacent to the superior vena cava at the bifurcation of the right and left brachiocephalic veins.

In some embodiments, the primary stent graft includes a tubular body having a proximal portion configured to couple with healthy arterial tissue proximal to an area of the vasculature to be treated, such as a diseased portion of the aorta. The proximal portion includes a bore defined by a wall. A pocket is disposed within the bore and longitudinally coupled to a wall of the bore. The pocket includes a lumen defined by a wall with a proximal end having a proximal opening, a closed distal end, and a distal opening disposed adjacent the closed distal end. The distal opening is disposed in a wall of the proximal portion of the tubular body wherein the lumen is in communication with an exterior of the proximal portion. A leg portion extends distally from the proximal portion and includes a bore defined by a wall in fluid communication with the bore of the proximal portion. The leg portion may be configured to be disposed within one of the iliac arteries branching from the aorta. A cross-sectional area of the bore of the leg portion may be equivalent or similar to a cross-sectional area of the lumen of the pocket. The secondary stent can include a tubular body. A proximal portion of the tubular body is disposable within the lumen of the pocket through the distal opening and configured to form a fluid seal with the wall of the pocket. A distal portion of the tubular body may extend from the distal opening and into a second iliac artery.

A method of manufacturing an embodiment of a bifurcated endovascular prosthesis within the scope of this disclosure may include the steps of constructing a primary stent graft construct comprising: obtaining a pocket mandrel and a first body mandrel; covering the pocket mandrel with a first polymeric covering; disposing the covered pocket mandrel within a groove of the body mandrel; covering the covered pocket mandrel and the body mandrel with a second polymeric covering; forming an opening in the first polymeric covering and the second polymeric covering adjacent a distal end of the pocket mandrel; and constructing a secondary stent graft construct comprising: obtaining a second body mandrel and covering the second body mandrel with a third polymeric covering. Other steps are contemplated.

A method of repairing a bifurcated blood vessel may include the steps of: deploying a primary stent graft of a bifurcated endovascular prosthesis in the bifurcated blood vessel, wherein a proximal portion of the primary stent graft is deployed adjacent a diseased portion of the bifurcated blood vessel and a distal portion of the primary stent graft is deployed in a first branch vessel; and deploying a secondary stent graft of the bifurcated endovascular prosthesis, wherein a proximal portion of the secondary stent graft is disposed within a pocket of the primary stent graft and a distal portion of the secondary stent graft is disposed within a second branch vessel. Other steps are contemplated within the scope of this disclosure. Deployment and treatment of other vessels or regions of the vasculature are likewise within the scope of this disclosure.

Embodiments may be understood by reference to the drawings, wherein like parts are designated by like numerals throughout. It will be understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

FIGS. 1A and 2-6B illustrate various views of an embodiment of a bifurcated endovascular prosthesis, related components, and related methods. FIG. 1B illustrates a perspective view of another embodiment of a bifurcated endovascular prosthesis. The related components and related methods discussed in FIGS. 2-6B may also apply to FIG. 1B. FIGS. 7-10 illustrate various views of another embodiment of a bifurcated endovascular prosthesis, related components, and related methods. FIGS. 11-16B illustrate various views of another embodiment of a bifurcated endovascular prosthesis, related components, and related methods. In certain views each bifurcated endovascular prosthesis may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

Figure 1B:
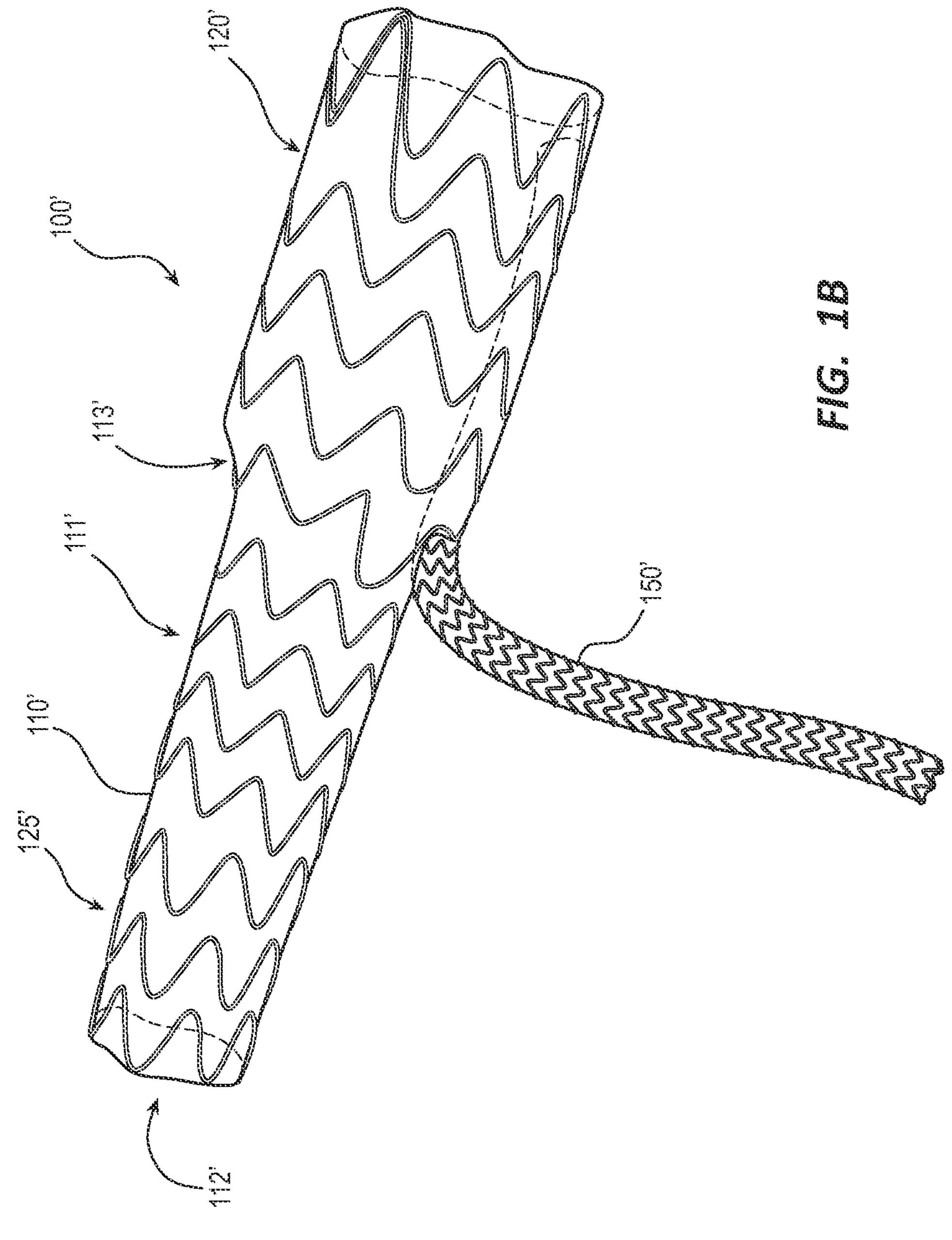
FIG. 1B is a perspective view of an embodiment of a bifurcated endovascular prosthesis.

FIG. 1A illustrates an embodiment of a bifurcated endovascular prosthesis 100. In the illustrated embodiment, the bifurcated endovascular prosthesis 100 is partially composed of a primary stent graft 110 and a secondary stent graft 150 selectively couplable to the primary stent graft 110. The primary stent graft 110 includes a body 111 having a proximal portion 120 and a distal portion 125. In the illustrated embodiment of FIG. 1A, the body 111 may be generally cylindered in shape and have a constant diameter from the proximal portion 120 to the distal portion 125.

FIG. 1B depicts an embodiment of a bifurcated endovascular prosthesis 100' that resembles the bifurcated endovascular prosthesis 100 described above and below in certain respects. Accordingly, like features are designated with like reference numerals, with an added apostrophe. For example, the embodiment depicted in FIG. 1B includes a primary stent graft 110' that may, in some respects, resemble the primary stent graft 110 of FIGS. 1A and 2-6B. Relevant disclosure set forth below regarding similarly identified features thus may not be discussed in regard to FIG. 1B. Moreover, specific features of bifurcated endovascular prosthesis 100' and related components shown in FIG. 1B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the bifurcated endovascular prosthesis 100' and related components depicted in FIG. 1B. Any suitable combination of the features, and variations of the same, described with respect to the bifurcated endovascular prosthesis 100 and related components illustrated in FIGS. 1 and 2-6B can be employed with the bifurcated endovascular prosthesis 100' and related components of FIG. 1B, and vice versa. This pattern of disclosure applies equally to further embodiments depicted in subsequent figures and described hereafter, wherein the leading digits may be further incremented.

FIG. 1B illustrates an embodiment of the bifurcated endovascular prosthesis 100'. In the illustrated embodiment, the bifurcated endovascular prosthesis 100' is partially composed of the primary stent graft 110' and a secondary stent graft 150' selectively couplable to the primary stent graft 110'. The primary stent graft 110' includes a body 111' having a proximal portion 120' and a distal portion 125'. In the illustrated embodiment of FIG. 1B, the distal portion 125' of the body 111' has an inward taper. The body 111' transitions from a greater diameter in the proximal portion 120' to a smaller diameter in the distal portion 125' at a transition point 113'. The inward taper of the distal portion 125' may allow for a guide wire (not shown) and a guide catheter (not shown) to manipulate around the body 111' prior to branching secondary stent graft 150'. The greater diameter of the proximal portion 120' creates space for the secondary stent graft 150' disposed within a bore 112' of the body 111'.

As illustrated, the embodiment of the bifurcated endovascular prosthesis 100 and 100' may be sized or otherwise configured to repair a diseased aorta vessel proximal to a bifurcation of iliac arteries. In various other embodiments, the bifurcated endovascular prosthesis 100 and 100' can be configured to repair any diseased arterial or venous vessel, including those including a bifurcation, such as a coronary artery, a carotid artery, a popliteal artery, a common femoral artery, brachiocephalic vein, etc. The bifurcated endovascular prosthesis 100 and 100' may be placed in the arterial vascular system such that blood flow through the bifurcated endovascular prosthesis 100 and 100' splits into two or more vessels. For example, the bifurcated endovascular prosthesis 100 and 100' may be deployed at a bifurcation between an aorta vessel and the left and right iliac vessels. The bifurcated endovascular prosthesis 100 and 100' may also be placed in the venous vascular system such that blood flow through the bifurcated endovascular prosthesis 100 and 100' converges into a single vessel from two or more vessels. For example, the bifurcated endovascular prosthesis 100 and 100' may be deployed at the bifurcation between a superior vena cava and left and right brachiocephalic vessels. As noted above, disclosure here regarding treatment of a specific region, such as the aorta, can be analogously applied to treatment of other portions of the vasculature or other lumens of the body.

Figures 2, 2A, 2B:
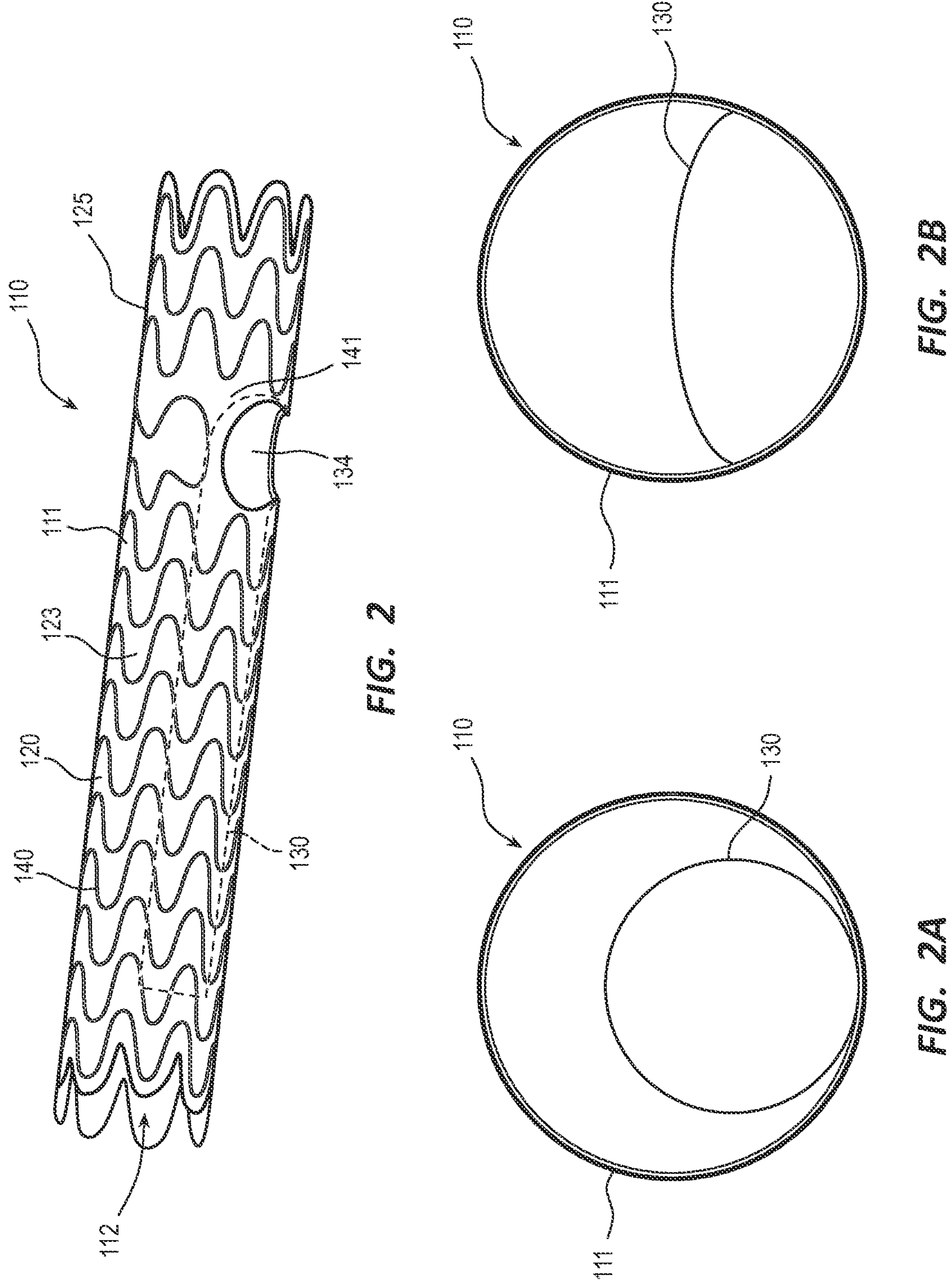
FIG. 2 is a perspective view of an embodiment of a primary stent graft of the bifurcated endovascular prosthesis of FIG. 1A.
FIG. 2A is an end view of one embodiment of the primary stent graft of FIG. 2 with a pocket having a circular cross-sectional shape.
FIG. 2B is an end view of another embodiment of the primary stent graft of FIG. 2 with a pocket having a D-shape cross-section.

FIG. 2 illustrates the primary stent graft 110 of the embodiment of FIG. 1A. The body 111 of the primary stent graft 110 may be generally cylindrical in shape having a bore 112 defined by a wall 123 extending through the proximal and distal portions 120, 125, such that blood can flow from the aorta, through the bore 112, and into an iliac artery when the bifurcated endovascular prosthesis 100 is implanted. The body 111 may be formed of a variety of materials and/or layers of materials, including biocompatible materials that are resistant to passage of blood through the wall 123. For example, the biocompatible material may be polyethylene terephthalate, polyurethane, silicone rubber, nylon, or fluoropolymer. Other biocompatible materials are contemplated within the scope of this disclosure. A thickness of the wall 123 may range from about 0.07 millimeter to about 0.5 millimeter.

In some embodiments, a length of the body 111 may range from about 50 mm to about 250 mm with a length of the proximal portion 120 ranging from about 20% to about 80% of the length of the primary stent graft 110. An outer diameter of the body 111 may range from about 18 millimeters to about 55 millimeters. In one embodiment, the body 111 may include a flared proximal end to facilitate sealing of the proximal portion 120 with a wall of the aorta and to prevent leakage of blood between the proximal portion 120 and the aorta wall. In some embodiments, the body 111 may include a cuff disposed adjacent the proximal portion 120 configured to facilitate sealing of the proximal portion 120 with the vessel wall and to prevent leakage of blood between the proximal portion 120 and the aorta wall. In other embodiments, the body 111 may include fixation features configured to prevent migration of the bifurcated endovascular prosthesis 100 relative to the aorta wall. The fixation features may include protruding barbs, sharpened protruding barbs, an adhesive, inflatable portions, strut hooks, etc.

Figure 3:
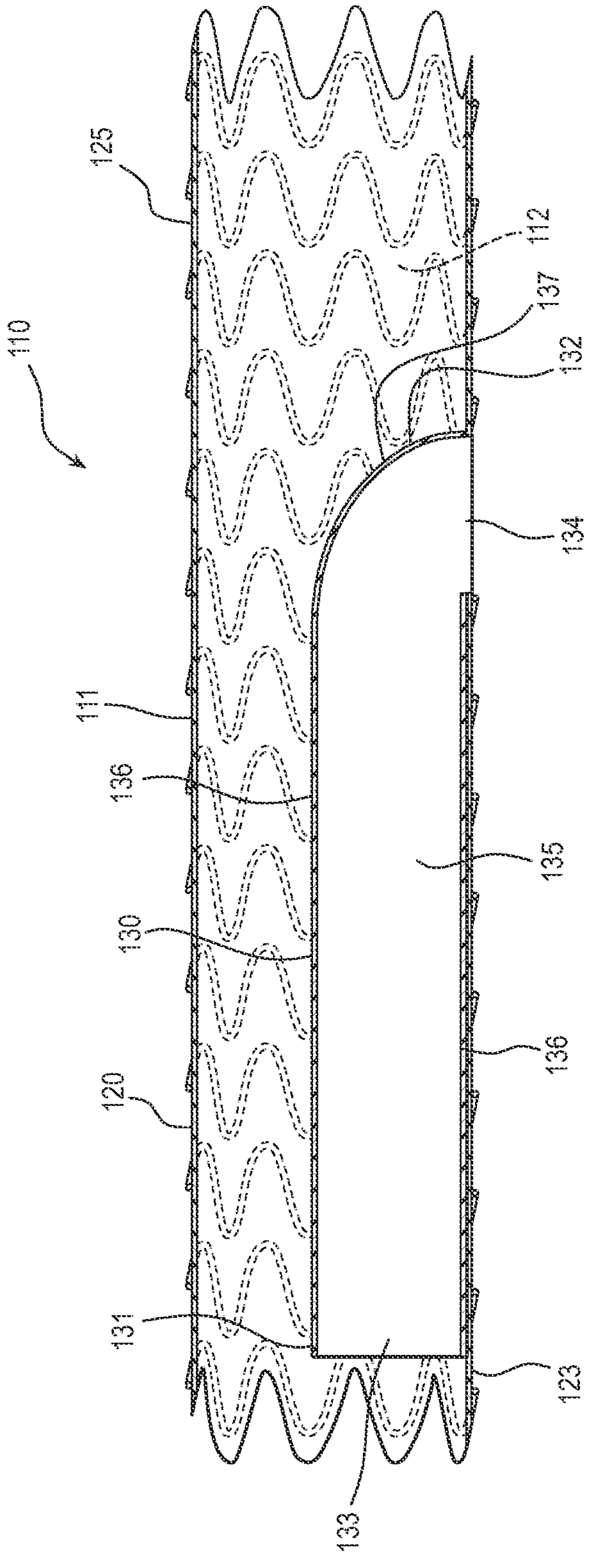
FIG. 3 is a longitudinal cross-sectional view of the primary stent graft of FIG. 2.

As shown in FIG. 3, the proximal portion 120 includes a pocket 130 disposed within the bore 112 and configured to receive the secondary stent graft 150. The pocket 130 is oriented such that it extends in a proximal direction along the wall 123 of the bore 112. A portion of a wall 136 of the pocket 130 may be coupled to the wall 123. The pocket 130 may be integrally formed with the wall 123 of the body 111. The proximal portion 120 and the pocket 130 may be formed to be an integral or unibody component such that there is not a seam or joint at a junction of the body 111 and the pocket 130. The pocket 130 includes a proximal end 131, a distal end 132, a proximal opening 133, a distal opening 134, and a lumen 135 defined by a wall 136. The pocket 130 may have a substantially round transverse cross-sectional shape, as shown in FIG. 2A. In another embodiment, a transverse cross-section of the pocket 130 may include a D-shape, as shown in FIG. 2B. In other embodiments, the pocket 130 may include any suitable transverse cross-sectional shape, such as oval, obround, semicircular, D-shaped, etc.

In some embodiments, the pocket 130 may be formed of the same material as the body 111 while in other embodiments these elements may be formed of different materials. A length of the pocket 130 may range from about 5 mm to about 50 mm. A thickness of the wall 136 may range from about 0.1 millimeter to about 0.9 millimeter and from about 0.21 millimeter to about 0.57 millimeter. The proximal end 131 of the pocket 130 is disposed distally of a proximal end of the body 111. The proximal opening 133 is disposed at the proximal end 131. The distal opening 134 is disposed adjacent the distal end 132 and in the wall 123 of the body 111. The lumen 135 extends from the proximal opening 133 to the distal opening 134. The lumen 135 may be configured to sealingly receive the secondary stent graft 150. A diameter of the lumen 135 may be equivalent to or smaller than an outer diameter of the secondary stent graft 150 such that an outer surface of the secondary stent graft 150 seals with an inner surface of the wall 136 of the pocket 130. In certain embodiments, the wall 136 may be circumferentially stretched when the secondary stent graft 150 is disposed within the lumen 135.

As shown in FIG. 3, the distal opening 134 of the pocket 130 may be disposed in the wall 123. The distal opening 134 is in fluid communication with the lumen 135 of the pocket 130 and with an exterior environment of the primary stent graft 110. In some embodiments, the distal opening 134 may be disposed at any location along a length of the proximal portion 120. A diameter of the distal opening 134 may be sized to receive the secondary stent graft 150. In other words, the distal opening 134 may be correlated to the secondary stent graft 150, for example, the diameter of the distal opening 134 may be equivalent to or smaller than an outer diameter of the secondary stent graft 150. The distal end 132 is closed. The distal end 132 may include an end wall 137 disposed at an angle ranging from about 30 degrees to about 90 degrees. The end wall 137 may be curved, as shown in FIG. 3. The distal opening 134 and the end wall 137 can be configured to allow the secondary stent graft 150 to extend radially outward from the primary stent graft 110 at an angle ranging from about zero degree to about 180 degrees.

As shown in FIG. 2, a wire scaffolding, framework, or stent such as wire stent 140 is shown to circumferentially surround the body 111. The wire stent 140 may be configured to radially expand the body 111 from a crimped or delivery configuration to an expanded or deployed configuration. When the bifurcated endovascular prosthesis 100 is deployed within a blood vessel, the body 111 may be pressed against a wall of the blood vessel. The wire stent 140 may be formed of any suitable material such as nickel-titanium alloy, stainless steel, platinum, polymers, etc. The wire stent 140 may have a zig-zag pattern, a wave pattern, or any other suitable pattern. An area 141 of the body 111 surrounding the distal opening 134 may be void of the wire stent 140. In the void area 141, the zig-zag pattern may loop back on itself to prevent the wire stent 140 from crossing over the distal opening 134. The wire stent 140 may be pre-formed or formed over the body 111. The material, pattern, and wire diameter of the wire stent 140 may be configured to provide a chronic radially outward directed force and a resistance to a radially inward directed force.

Figure 4:
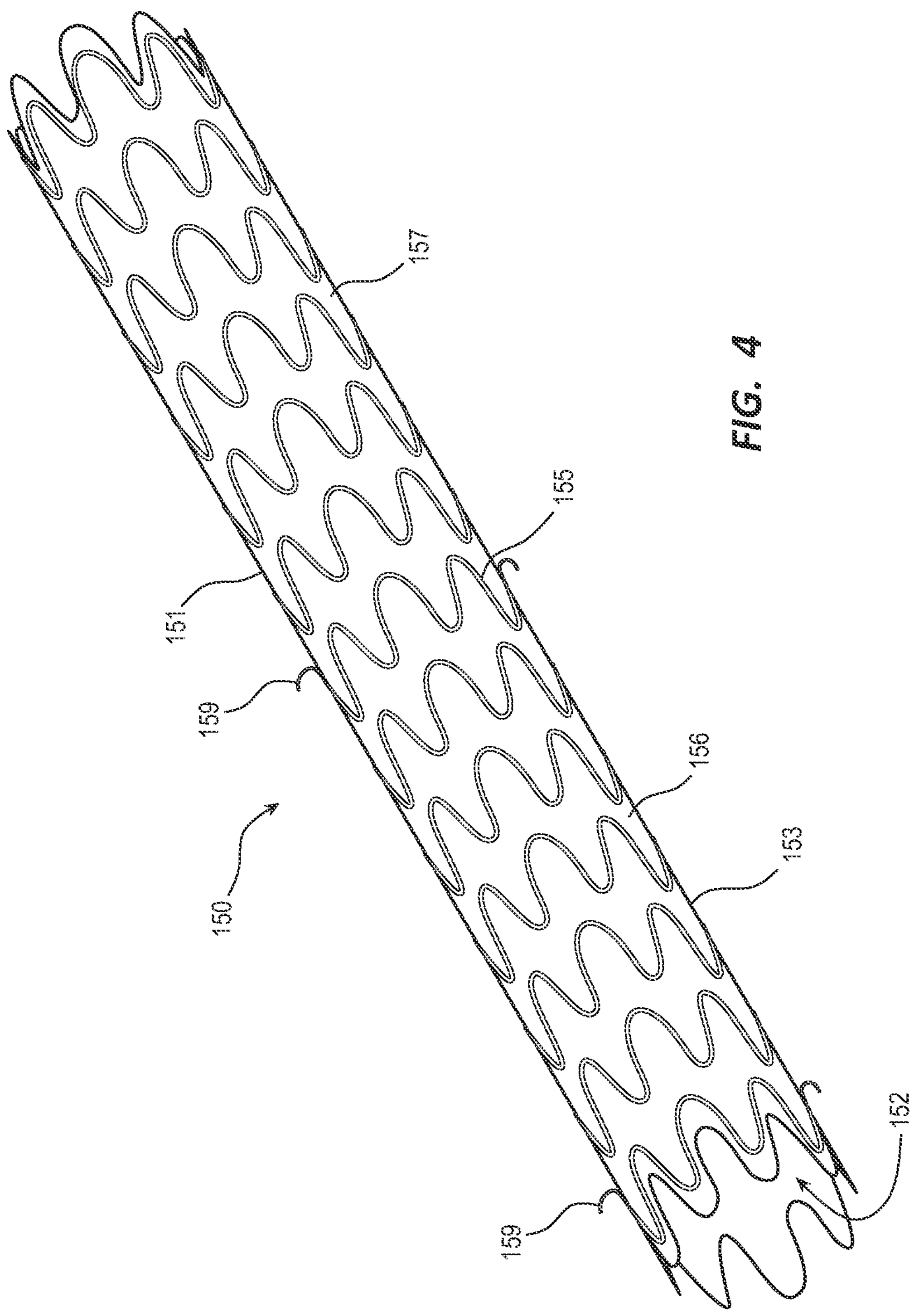
FIG. 4 is a perspective view of an embodiment of a secondary stent graft of the bifurcated endovascular prosthesis of FIG. 1A.

FIG. 4 illustrates an embodiment of the secondary stent graft 150. As illustrated, the secondary stent graft 150 includes a body 151 including a proximal portion 156 and a distal portion 157. The body 151 may be generally cylindrical in shape having a bore 152 defined by a wall 153 such that blood can flow from the aorta, through the bore 152, and into an iliac artery when the bifurcated endovascular prosthesis 100 is implanted. A cross-sectional area of the bore 152 may be substantially equivalent to a cross-sectional area of the bore 112 of the primary stent graft 110. This configuration facilitates substantially equivalent blood flow rates through the bores 112, 152 such that blood flow to the iliac arteries is substantially equivalent.

The body 151 may be formed of a variety of materials and/or layers of materials, including biocompatible materials that are resistant to passage of blood through the wall 153. For example, the biocompatible material may be polyethylene terephthalate, polyurethane, silicone rubber, nylon, or fluoropolymer. Other biocompatible materials are contemplated within the scope of this disclosure. A thickness of the wall 153 may range from about 0.1 millimeter to about 0.9 millimeter and from about 0.21 millimeter to about 0.57 millimeter.

In some embodiments, a length of the body 151 may range from about 20 millimeters to about 250 millimeters. An outer diameter of the body 151 may range from about 3 millimeters to about 55 millimeters. In some embodiments, the body 151 may include fixation features 159 configured to prevent migration of the secondary stent graft 150 relative to the primary stent graft 110. For example, in one embodiment, the fixation features 159 may be disposed at a proximal end of the body 151 to couple with the proximal end 131 of the pocket 130 to prevent the secondary stent graft 150 from distal migration or distal axial movement relative to the primary stent graft 110. In another embodiment, the fixation features 159 may be disposed at a mid-portion of the body 151 to couple with the body 111 adjacent the distal opening 134 to prevent the secondary stent graft 150 from proximal migration or proximal axial movement relative to the primary stent graft 110. The fixation features 159 may include protruding barbs, sharpened protruding barbs, an adhesive, inflatable portions, flared portions, strut hooks, or any combination thereof, etc. In some embodiments, the pocket 130 includes the fixation features 159 to engage the secondary stent graft 150 to prevent distal and/or proximal migration or movement of the secondary stent graft 150 relative to the primary stent graft 110

In certain embodiments, the lumen 135 of the pocket 130 can be inwardly tapered from the proximal end 131 to the distal end 132 and the secondary stent graft 150 can be inwardly tapered along the proximal portion 156 to prevent distal migration of the secondary stent graft 150 relative to the primary stent graft 110. In another embodiment, the body 151 may include a step transition from a larger diameter proximal portion 156 to a smaller diameter distal portion 157. The pocket 130 may include a corresponding step transition to receive the step transition of the body 151 to prevent distal migration of the secondary stent graft 150 relative to the primary stent graft 110.

A wire scaffolding, framework, or stent such as wire stent 155 is shown to circumferentially surround the body 151. The wire stent 155 may be configured to radially expand the body 151 from a crimped or delivery configuration to an expanded or deployed configuration. When the bifurcated endovascular prosthesis 100 is deployed, the proximal portion of the body 151 may be pressed against the wall 136 of the pocket 130 and a distal portion of the body 151 may be pressed against a wall of the iliac artery. The wire stent 155 may be formed of any suitable material, such as nickel-titanium alloy, stainless steel, platinum, polymers, etc. The wire stent 155 may have a zig-zag pattern, a wave pattern, or any other suitable pattern. The wire stent 155 may be pre-formed or formed over the body 151. The material, pattern, and wire diameter of the wire stent 155 may be configured to provide a chronic radially outward directed force and a resistance to a radially inward directed force. In some embodiments, the wire stent 155 may include one, two, three, or more lumens.

FIGS. 5A-5D illustrate a method of manufacturing the primary stent graft 110. FIG. 5A depicts a body forming mandrel 160 and a pocket forming mandrel 170. The body forming mandrel 160 includes a slot or groove 161 configured to receive the pocket forming mandrel 170. The body forming mandrel 160 is generally cylindrical in shape and formed from any suitable material, such as stainless steel, aluminum, etc. The pocket forming mandrel 170 includes a convex shaped outer surface 171, wherein a curvature of the outer surface 171 corresponds with a curvature of an outer surface 162 of the body forming mandrel 160. The pocket forming mandrel 170 further includes a convex shaped inner surface 172. A cross-section of the pocket forming mandrel 170 includes an eye shape. The slot 161 includes a concave shape having a curvature to correspond to a curvature of the inner surface 172. As illustrated, a distal end 173 of the pocket forming mandrel 170 includes a radius. In other embodiments, the distal end 173 may be angled squared off, pointed, etc.

As depicted in FIG. 5B, a polymeric covering 174 surrounds the pocket forming mandrel 170. The covering 174 will be the wall 136 of the pocket 130 of the bifurcated endovascular prosthesis 100, as previously described. The material of the wall 136 is previously described. The covering 174 can be applied using any suitable technique. For example, the covering 174 can be applied by wrapping strips of material around the mandrel, serially depositing material onto the mandrel, dipping the mandrel into a solvent based polymer solution, or spraying the mandrel with a solvent based polymer solution. Other application techniques are contemplated. As the arrows of FIG. 5B indicate, during manufacturing, the covered pocket forming mandrel 170 may be disposed within the slot 161.

As shown in FIG. 5C, a polymeric covering 163 is disposed around the body forming mandrel 160 and the covered pocket forming mandrel 170 that has been disposed in slot 161. The covering 163 is configured to be the wall 123 of the body 111 of the primary stent graft 110 as previously described. The covering 163 can be applied using any suitable technique. For example, the covering 163 can be applied by wrapping strips of material around the mandrel, serially depositing material onto the mandrel, dipping the mandrel into a solvent based polymer solution, or spraying the mandrel with a solvent based polymer solution. Other application techniques are contemplated.

As illustrated in FIG. 5D, an opening 164 is formed in the covering 163. The opening 164 is configured to be the distal opening 134 of the pocket 130 as previously described. The opening 164 can be formed using any suitable technique. For example, the opening 164 can be formed by cutting with a die, blade or laser. Other forming techniques are contemplated. In certain embodiments, the distal end 173 of the pocket forming mandrel 170 may be used as a guide or reference mark to form the opening 164. In other embodiments, the opening 164 is formed following removal of the pocket forming mandrel 170.

The wire stent 140 may be disposed over the covered body and pocket forming mandrels 160, 170 and oriented such that the void area 141 surrounds the opening 164. An outer polymeric covering may be disposed over the wire stent 140. The covered wire stent 140 and covered body and pocket forming mandrels 160, 170 may be sintered at about 385 degrees Centigrade to bind the coverings and the wire stent 140 together. The body and pocket forming mandrels 160, 170 are removed from the body 111 and the pocket 130, respectfully.

Figure 6B:
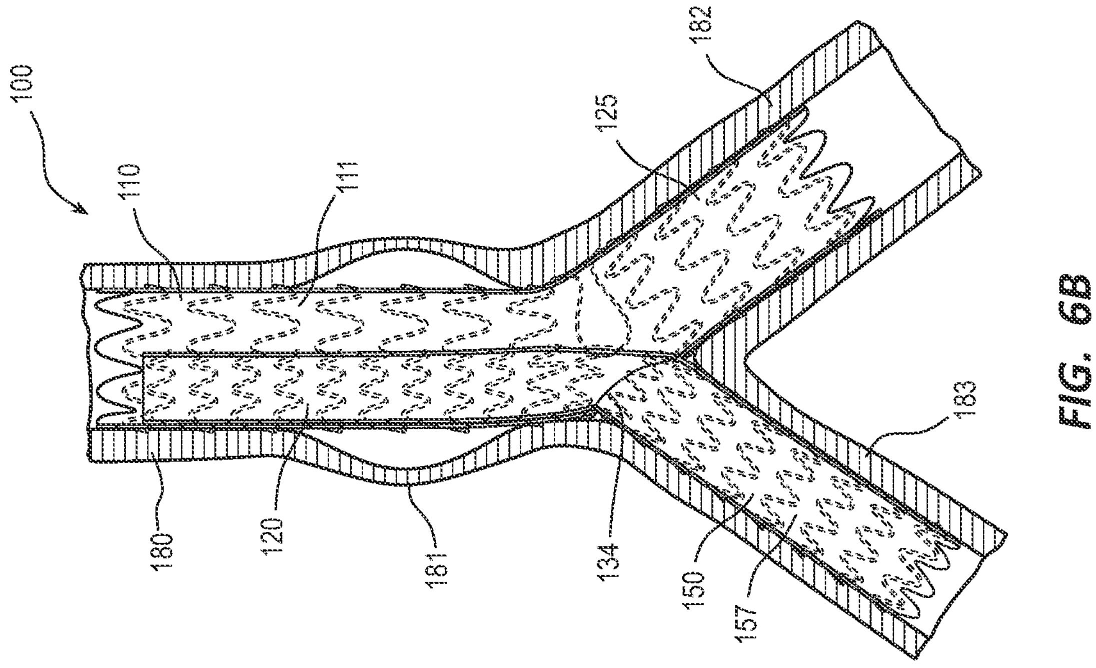
FIG. 6B is a longitudinal cross-sectional view of the bifurcated endovascular prosthesis of FIG. 1A disposed in the diseased aorta.
Figure 6A:
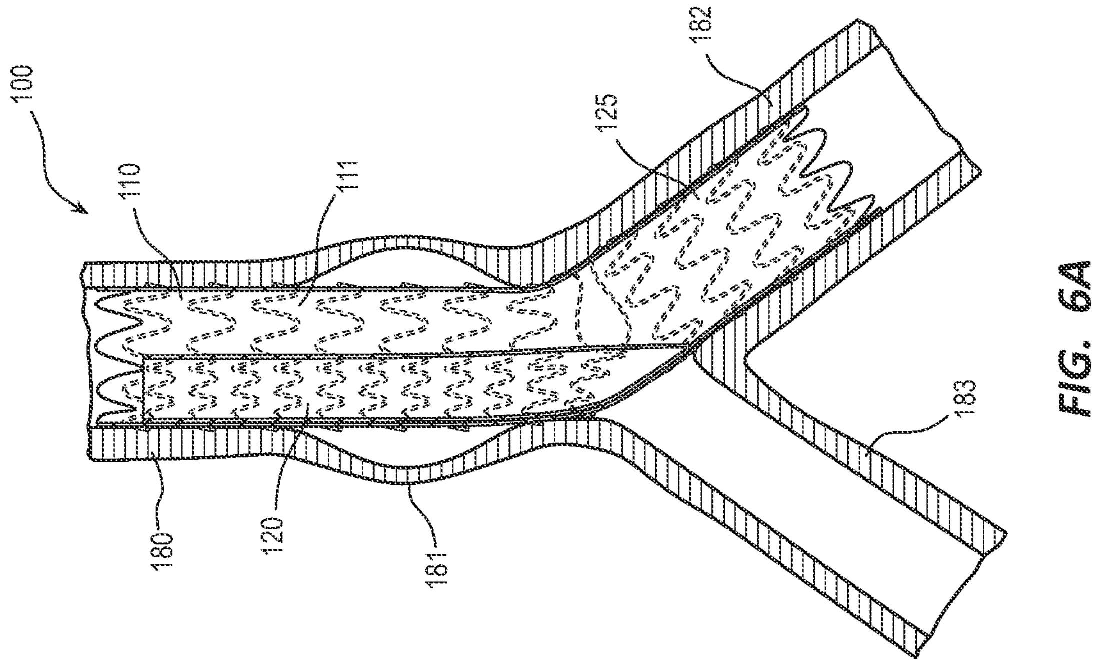
FIG. 6A is a longitudinal cross-sectional view of the primary stent graft of FIG. 1A disposed in a diseased aorta.

FIGS. 6A and 6B illustrate a method of implanting the bifurcated endovascular prosthesis 100 in a diseased blood vessel (e.g., aorta) and iliac arteries. FIG. 6A shows the primary stent graft 110 of the bifurcated endovascular prosthesis 100 deployed in the aorta 180. The primary stent graft 110 may be deployed using a delivery catheter system, wherein the primary stent graft 110 is radially compressed and disposed within the delivery catheter system. The body 111 may be radially expanded (e.g., self-expanded or balloon expanded) to compress the proximal portion 120 against a healthy tissue section of a wall of the aorta 180 proximal to a diseased section 181 of the aorta 180 such that the bifurcated endovascular prosthesis 100 may be secured in place. The diseased section 181 may be an aneurysm, a pseudoaneurysm, an aortic dissection, a stenosis, or any other type of vascular disease. The distal portion 125 may extend distally into a first iliac artery 182 and may be radially expanded to compress against a wall of the first iliac artery 182.

FIG. 6B shows the secondary stent graft 150 deployed and coupled to the primary stent graft 110. The secondary stent graft 150 may be deployed using a delivery catheter system, wherein the secondary stent graft 150 is radially compressed and disposed within the delivery catheter system. A proximal portion 156 is disposed within the pocket 130 and a distal portion 157 extends through the distal opening 134 and into the second iliac artery 183. The secondary stent graft 150 may be radially expanded (e.g., self-expanded or balloon expanded) to compress the proximal portion 156 against the wall 136 of the pocket 130 and the distal portion 157 against a wall of the second iliac artery 183 to form a fluid tight seal and to secure the secondary stent graft 150 in place. When the bifurcated endovascular prosthesis 100 is fully deployed, as shown in FIG. 6B, blood can flow from the aorta 180, into the primary stent graft 110. Within the primary stent graft 110 the blood flow is divided into two flows, a first flow continues through the primary stent graft 110 and exits into the first iliac artery 182, and the second flow enters the secondary stent graft 150, flows through the secondary stent graft 150, and exits into the second iliac artery 183. The blood flows into the first and second iliac arteries 182, 183 can be substantially equivalent. In other embodiments, the bifurcated endovascular prosthesis 100 may include more than two lumens and the blood flow in each of the lumens may be substantially equivalent or may be different depending on a size of blood vessel the lumen is in fluid communication with.

FIGS. 7-10 depict an embodiment of a bifurcated endovascular prosthesis 200 that resembles the bifurcated endovascular prosthesis 100 described above in certain respects. Accordingly, like features are designated with like reference numerals, with the leading digit incremented to "2." For example, the embodiment depicted in FIGS. 7-10 includes a primary stent graft 210 that may, in some respects, resemble the primary stent graft 110 of FIG. 1A. Relevant disclosure set forth above regarding similarly identified features thus may not be repeated hereafter. Moreover, specific features of the bifurcated endovascular prosthesis 100 and related components shown in FIGS. 1-6B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the bifurcated endovascular prosthesis 200 and related components depicted in FIGS. 7-10. Any suitable combination of the features, and variations of the same, described with respect to the bifurcated endovascular prosthesis 100 and related components illustrated in FIGS. 1-6B can be employed with the bifurcated endovascular prosthesis 200 and related components of FIGS. 7-10, and vice versa. This pattern of disclosure applies equally to further embodiments depicted in subsequent figures and described hereafter, wherein the leading digits may be further incremented.

Figure 7:
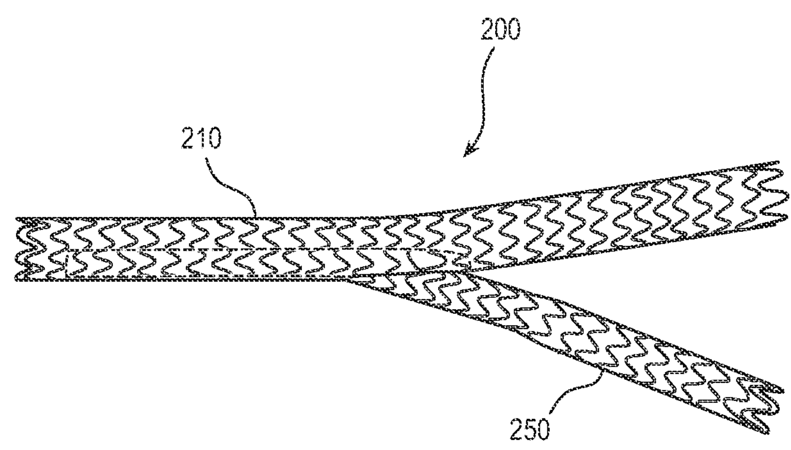
FIG. 7 is a perspective view of another embodiment of a bifurcated endovascular prosthesis.

FIG. 7 illustrates an embodiment of a bifurcated endovascular prosthesis 200. In the illustrated embodiment, the bifurcated endovascular prosthesis 200 is partially composed of a primary stent graft 210 and a secondary stent graft 250 selectively coupled to the primary stent graft 210.

Figure 8:
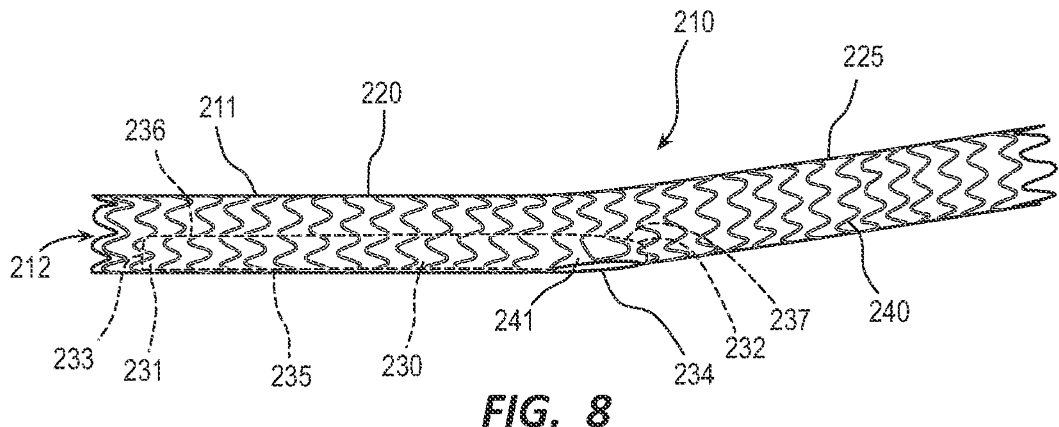
FIG. 8 is a perspective view of an embodiment of a primary stent graft of the bifurcated endovascular prosthesis of FIG. 7.

As depicted in FIG. 8, the primary stent graft 210 includes a body 211 having a proximal portion 220, a distal portion 225, and a bore 212 extending therethrough. In some embodiments, a length of the body 211 may range from about 20 millimeters to about 250 millimeters with a length of the proximal portion 220 ranging from about 20% to about 80% of the length of the primary stent graft 210. An outer diameter of the body 211 may range from about 3 millimeters to about 55 millimeters. In the illustrated embodiment, the proximal portion 220 includes a pocket 230 disposed within the bore 212 and configured to receive the secondary stent graft 250. The pocket 230 includes a proximal end 231, a distal end 232, a proximal opening 233, a distal opening 234, and a lumen 235 defined by a wall 236. A length of the pocket 230 may range from about 10% to about 90% of the length of the proximal portion 220. A thickness of the wall 236 may range from about 0.1 millimeter to about 0.9 millimeter and from about 0.21 millimeter to about 0.57 millimeter. The proximal opening 233 is disposed at the proximal end 231. The distal opening 234 is disposed adjacent the distal end 232 and in the wall 236 of the body 211. The distal end 232 is closed. The lumen 235 extends from the proximal opening 233 to the distal opening 234.

The distal end 232 may include an end wall 237 disposed at an angle ranging from about 30 degrees to about 90 degrees. The distal opening 234 and the distal end 232 can be configured to allow the secondary stent graft 250 to extend radially outward from the body 211 at an angle ranging from about 30 degrees to about 90 degrees. When outside of the body 211, the secondary stent graft 250 may be configured to bend at an angle ranging from about zero degree to about 180 degrees.

A wire scaffolding, framework, or stent such as wire stent 240 is shown to circumferentially surround the body 211. The wire stent 240 may be configured to radially expand the body 211 from a crimped or delivery configuration to an expanded or deployed configuration. An area 241 of the body 211 surrounding the distal opening 234 may be void of the wire stent 240. In the void area 241, a zig-zag pattern may loop back on itself to prevent the wire stent 240 from crossing over the distal opening 234.

Figure 9:
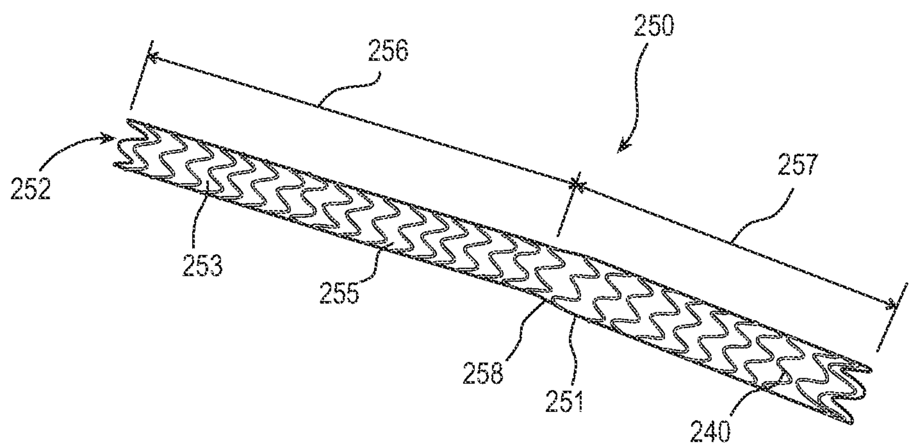
FIG. 9 is a perspective view of an embodiment of a secondary stent graft of the bifurcated endovascular prosthesis of FIG. 7.

FIG. 9 illustrates an embodiment of the secondary stent graft 250. As illustrated, the secondary stent graft 250 includes a body 251 having a proximal portion 256 and a distal portion 257. The body 211 may be generally cylindrical in shape having a bore 252 defined by a wall 253. A thickness of the wall 253 may range from about 0.1 millimeter to about 0.9 millimeter and from about 0.21 millimeter to about 0.57 millimeter. In an embodiment, a cross-sectional area of the bore 252 may be substantially equivalent to a cross-sectional area of the bore 212 of the primary stent graft 210. This configuration facilitates substantially equivalent blood flow rates through the bores 212, 252. In some embodiments, the cross-sectional area of the bore 252 may be smaller or larger than the cross-sectional area of the bore 212, such that a blood flow rate through the bore 252 is lesser than or greater than, respectively, a blood flow rate through the bore 212.

In some embodiments, a length of the body 251 may range from about 20 millimeters to about 250 millimeters. An outer diameter of the proximal portion 256 may range from about 3 millimeters to about 55 millimeters. An outer diameter of the distal portion 257 may range from about 3 millimeters to about 55 millimeters. A taper portion 258 may be disposed between the proximal portion 256 and the distal portion 257. A wire scaffolding, framework, or stent such as wire stent 255 is shown to circumferentially surround the body 251. The wire stent 255 may be configured to radially expand the body 251 from a crimped or delivery configuration to an expanded or deployed configuration.

Figure 10:
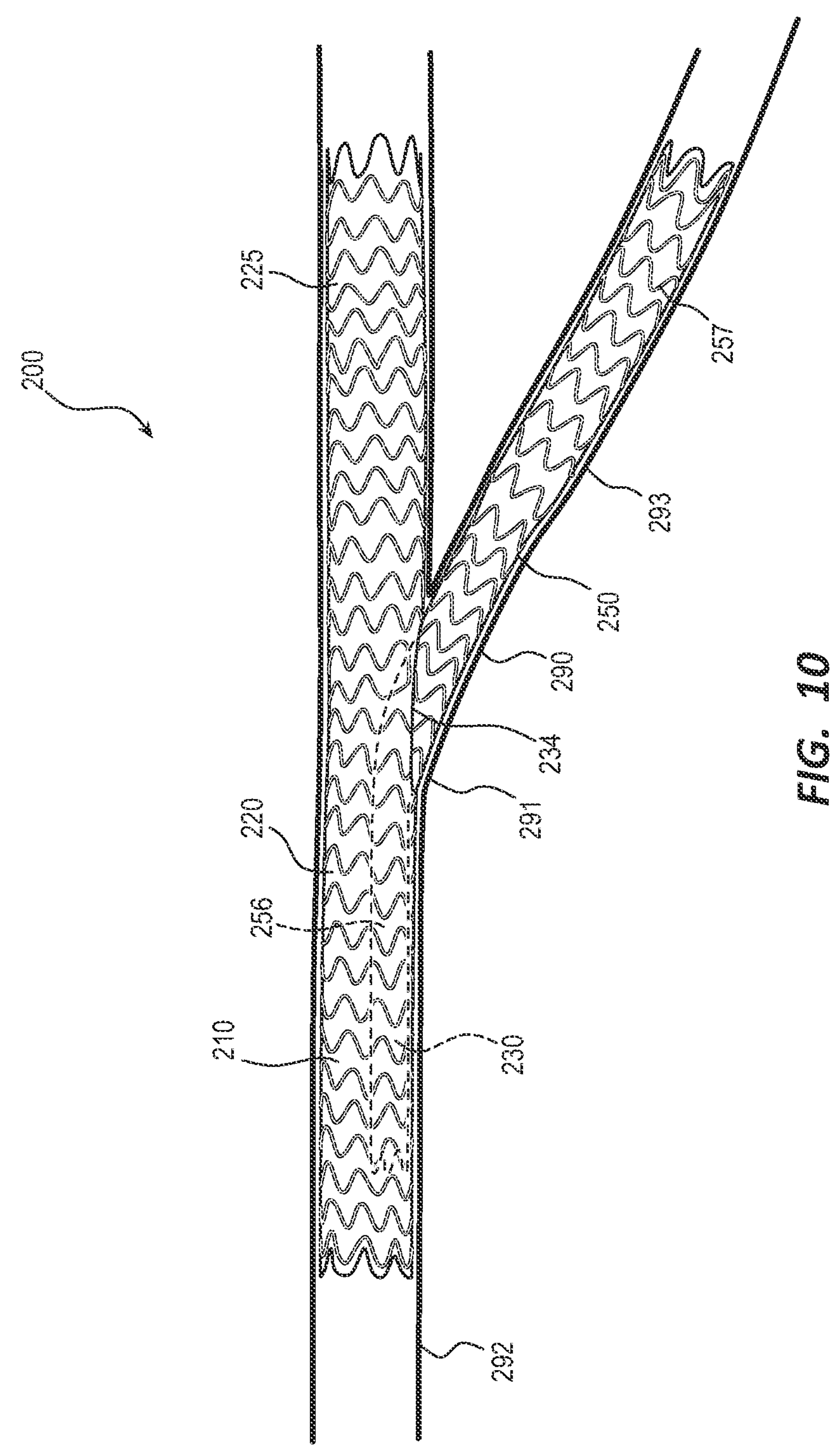
FIG. 10 is a side view of the bifurcated endovascular prosthesis of FIG. 7 disposed within vessels adjacent an anastomosis.

FIG. 10 illustrates the bifurcated endovascular prosthesis 200 deployed adjacent an arteriovenous (AV) fistula 290. The AV fistula 290 may be utilized to provide vascular access for hemodialysis treatments of patients with end stage renal disease or other kidney failure. In various embodiments, the bifurcated endovascular prosthesis 200 may be utilized to either create or repair the AV fistula 290. As illustrated, the primary stent graft 210 is disposed within an artery 292. The artery 292 may be any artery within the patient's body that is suitable to be anastomosed or connected to an adjacent vein to form the AV fistula 290. For example, the artery may be a radial artery, an ulnar artery, a brachial artery, a femoral artery, etc. The primary stent graft 210 is positioned with the proximal portion 220 proximal to an anastomosis 291 of the artery 292 and a vein 293 and the distal portion 225 distal to the anastomosis 291. The proximal portion 220 is directed upstream such that blood can flow into the proximal portion 220 and the secondary stent graft 250. The distal opening 234 of the pocket 230 is disposed at the anastomosis 291. The secondary stent graft 250 extends from the primary stent graft 210 through the anastomosis 291 into the vein 293. The proximal portion 256 of the secondary stent graft 250 is disposed within the pocket 230 and the distal portion 257 is disposed in the vein 293. In other embodiments, the primary stent graft 210 can be deployed in the artery 292 and the secondary stent graft 250 can be deployed in the vein 293 such that the secondary stent graft 250 extends through a wall of the vein 293, through a wall of the artery 292 and into the pocket 230 to create an AV fistula.

When the bifurcated endovascular prosthesis 200 is deployed as shown in FIG. 10, blood can flow from the artery 292 proximal to the bifurcated endovascular prosthesis 200 into the bifurcated endovascular prosthesis 200 where the blood flow can be split into a first blood flow that continues through the bifurcated endovascular prosthesis 200 and into the artery 292 distal to the bifurcated endovascular prosthesis 200 and a second blood flow that flows through the secondary stent graft 250 and into the vein 293.

Figure 11:
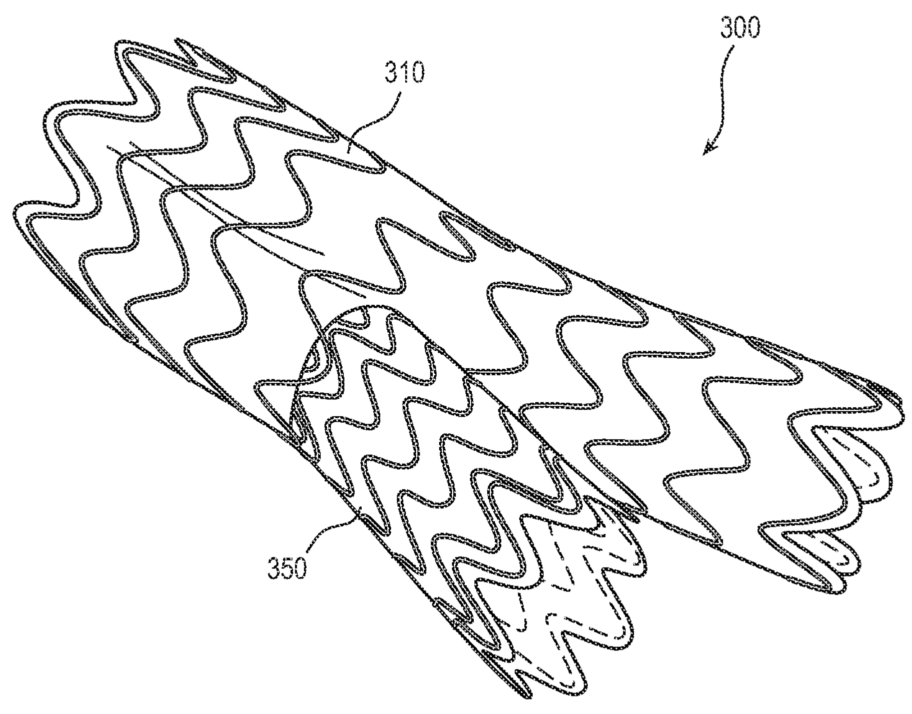
FIG. 11 is a perspective view of another embodiment of a bifurcated endovascular prosthesis.

FIG. 11 illustrates an embodiment of another bifurcated endovascular prosthesis 300. In the illustrated embodiment, the bifurcated endovascular prosthesis 300 is partially composed of a primary stent graft 310 and a secondary stent graft 350 selectively coupled to the primary stent graft 310.

Figure 12B:
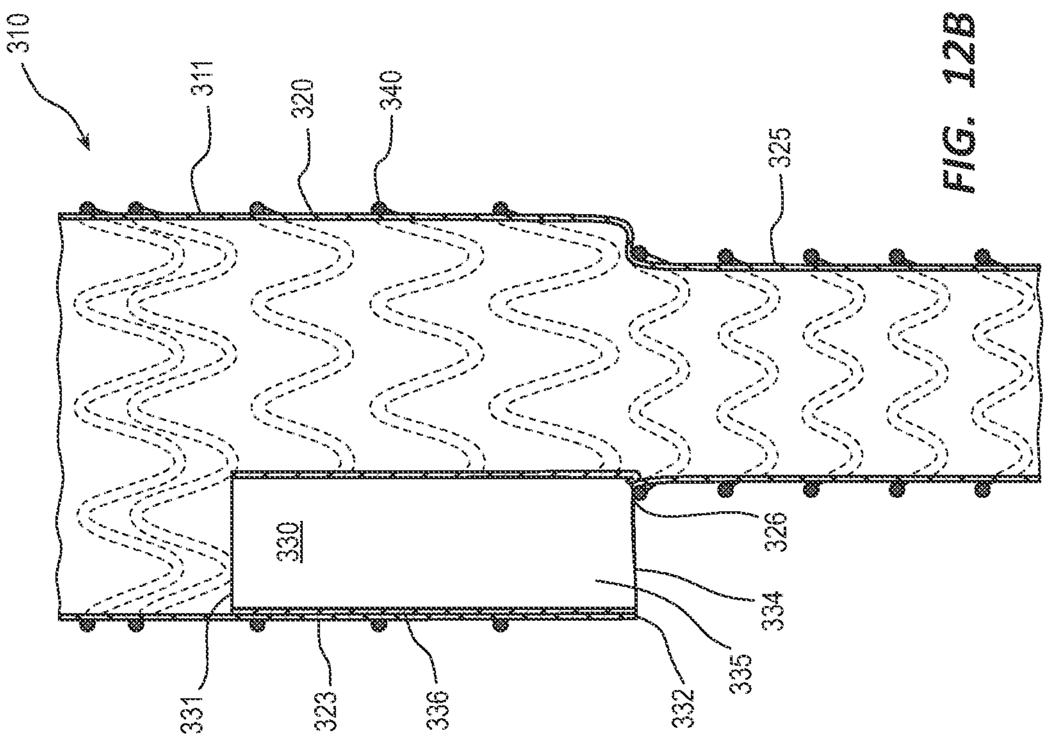
FIG. 12B is a longitudinal cross-sectional view of the primary stent graft of FIG. 12A.
Figure 12A:
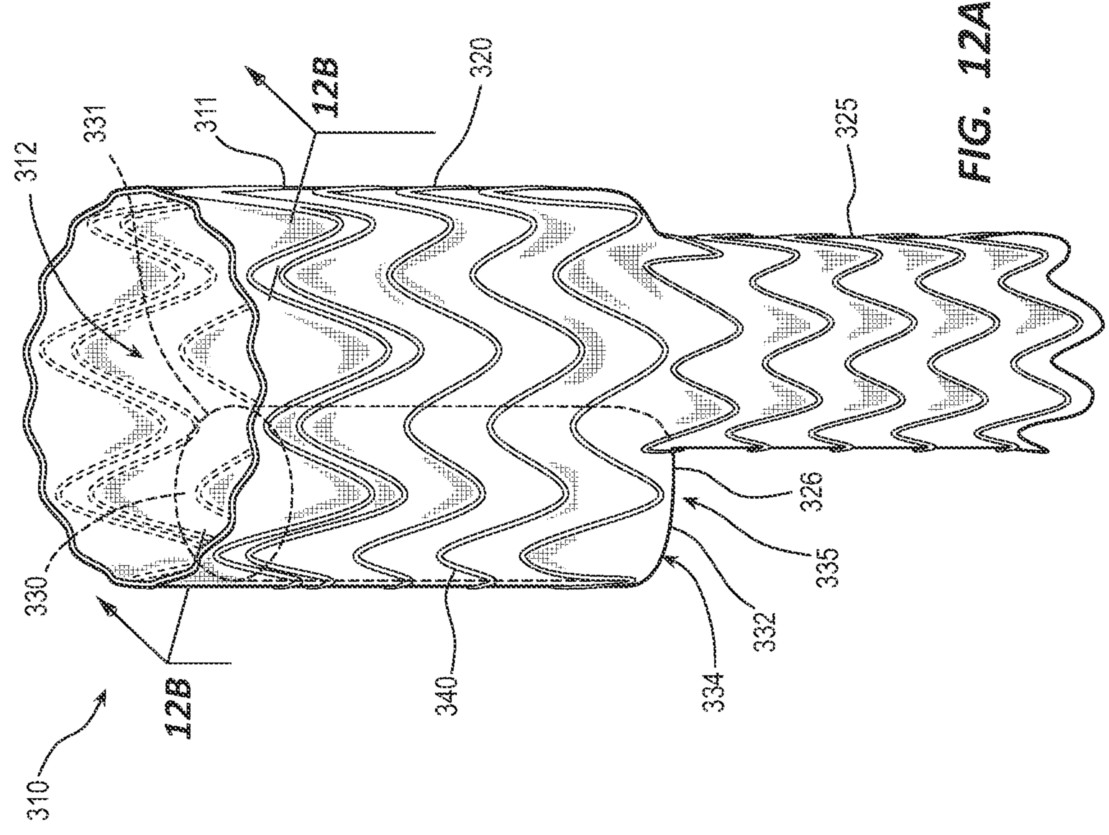
FIG. 12A is a perspective view of an embodiment of a primary stent graft of the bifurcated endovascular prosthesis of FIG. 11.

As depicted in FIGS. 12A and 12B, the primary stent graft 310 includes a body 311 having a proximal portion 320, a distal portion 325, and a bore 312 defined by a wall 323 extending therethrough. In some embodiments, a length of the body 311 may range from about 20 millimeters to about 250 millimeters with a length of the proximal portion 320 ranging from about 20% to about 80% of the length of the primary stent graft 310. An outer diameter of the proximal portion 320 may range from about 20 millimeters to about 55 millimeters and an outer diameter of the distal portion 325 may range from about 10 millimeters to about 28 millimeters.

In the illustrated embodiment, the proximal portion 320 includes a sleeve 330 disposed within the bore 312 and configured to receive the secondary stent graft 350. The sleeve 330 includes a proximal end 331, a distal end 332, a distal opening 334, and a lumen 335 defined by a wall 336. A length of the sleeve 330 may range from about 10% to about 90% of a length of the proximal portion 320. A thickness of the wall 336 may range from about 0.1 millimeter to about 0.9 millimeter and from about 0.21 millimeter to about 0.57 millimeter. A portion of the wall 336 is coupled to the wall 323 of the body 311. The distal opening 334 is disposed at the distal end 332 and in a distally facing portion 326 of the body 311. The lumen 335 extends from the proximal end 331 to the distal opening 334. The proximal end 331 is closed. A cross-sectional area of the lumen 335 may be substantially equivalent to a cross-sectional area of the bore 312 through the distal portion 325 of the body 311. The sleeve 330 can be configured to collapse against the wall 323 when the primary stent graft 310 is in a crimped or delivery configuration. A wire scaffolding, framework, or stent such as wire stent 340 is shown to circumferentially surround the body 311. The wire stent 340 may be configured to radially expand the body 311 from the crimped or delivery configuration to an expanded or deployed configuration.

Figure 13:
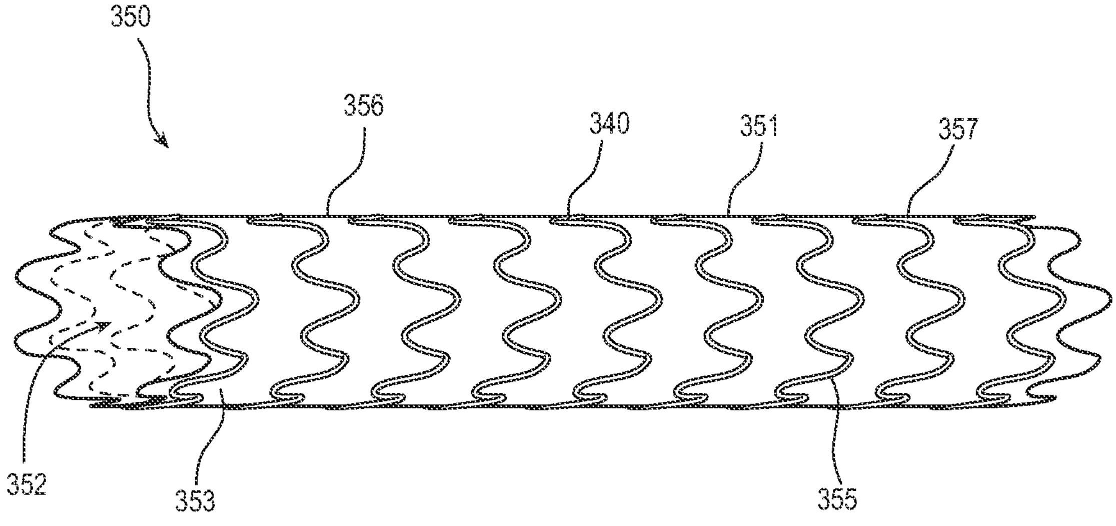
FIG. 13 is a perspective view of an embodiment of a secondary stent graft of the bifurcated endovascular prosthesis of FIG. 11.

FIG. 13 illustrates an embodiment of the secondary stent graft 350. As illustrated, the secondary stent graft 350 includes a body 351 having a proximal portion 356 and a distal portion 357. The body 351 may be generally cylindrical in shape having a bore 352 defined by a wall 353. A thickness of the wall 353 may range from about 0.1 millimeter to about 0.9 millimeter and from about 0.21 millimeter to about 0.57 millimeter. In an embodiment, a cross-sectional area of the bore 352 may be substantially equivalent to a cross-sectional area of the bore 312 of the primary stent graft 310. This configuration facilitates substantially equivalent blood flow rates through the bores 312, 352. In some embodiments, the cross-sectional area of the bore 352 may be smaller or larger than the cross-sectional area of the bore 312, such that a blood flow rate through the bore 352 is lesser than or greater than, respectively, a blood flow rate through the bore 312.

In some embodiments, a length of the body 351 may range from about 30 millimeters to about 250 millimeters. An outer diameter of the body 351 may range from about 7.5 millimeters to about 25.2 millimeters wherein the body 351 may be configured to be oversized relative to the bore 312 of the primary stent graft 310. A wire scaffolding, framework, or stent such as wire stent 355 is shown to circumferentially surround the body 351. The wire stent 355 may be configured to radially expand the body 351 from a crimped or delivery configuration to an expanded or deployed configuration.

Figure 14A:
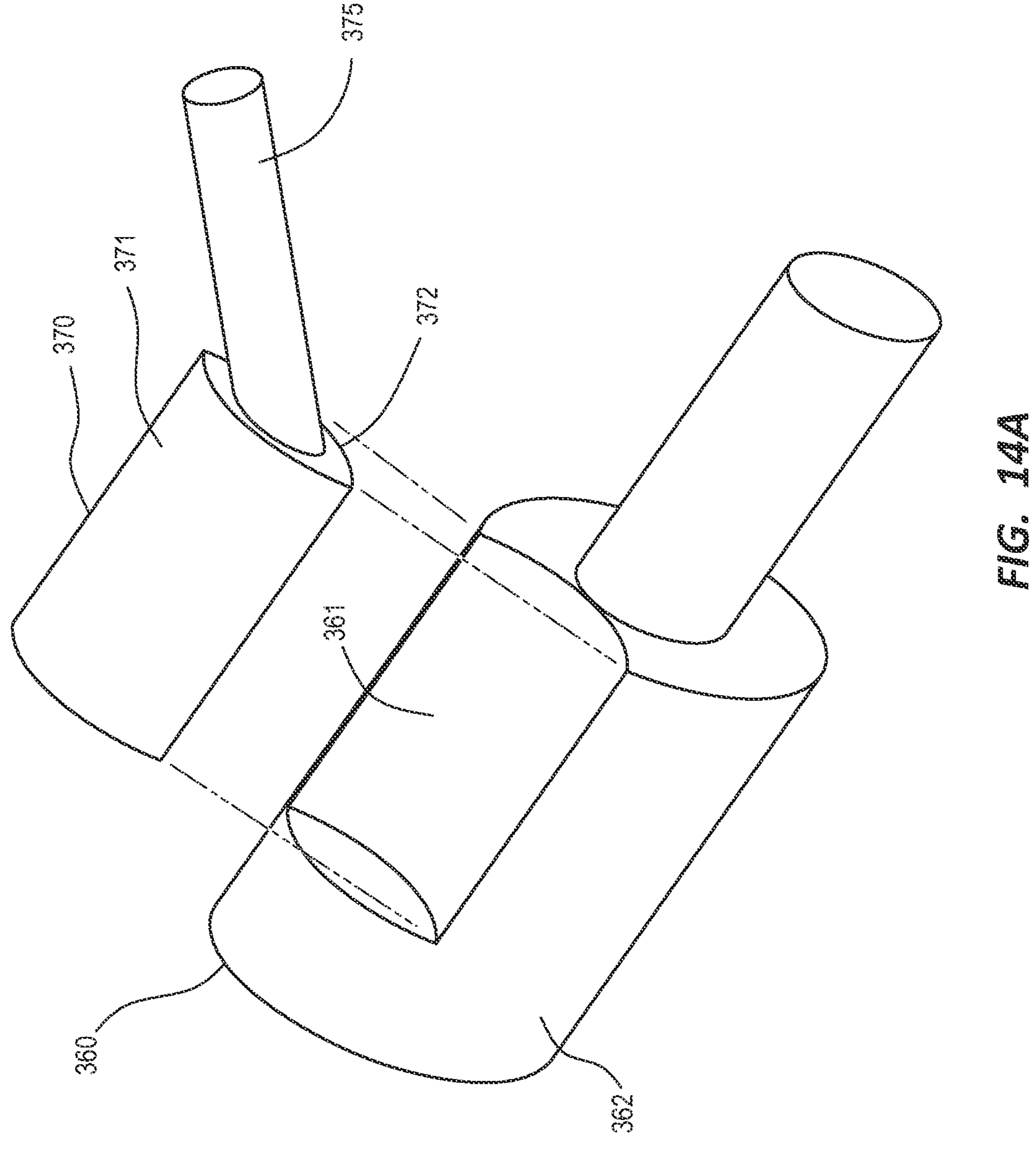
FIG. 14A is a perspective view of embodiments of a body mandrel and a sleeve mandrel.
Figure 14B:
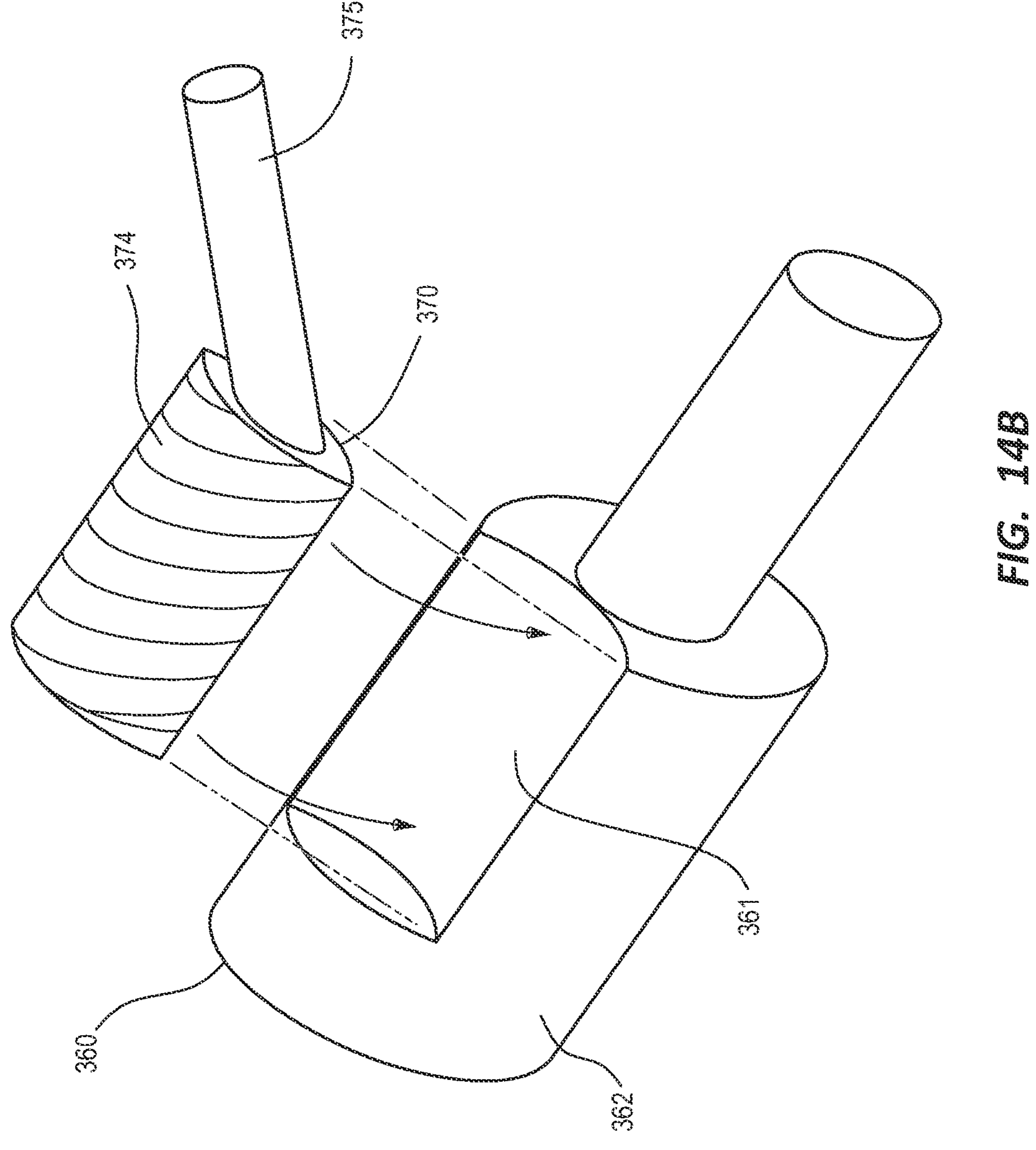
FIG. 14B is a perspective view of the sleeve mandrel of FIG. 14A covered with a polymeric covering.
Figure 14C:
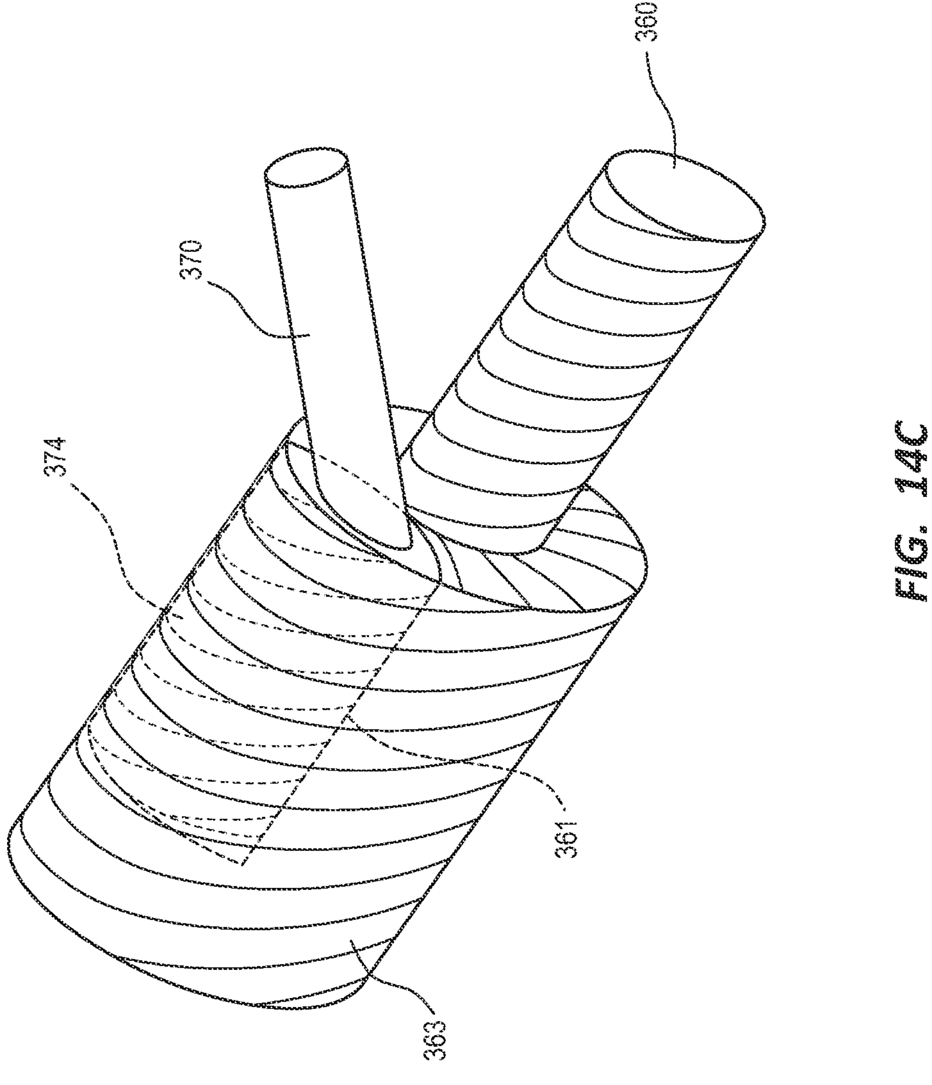
FIG. 14C is a perspective view of the polymeric covered sleeve mandrel of FIG. 14B coupled to the body mandrel of FIG. 14B and the body mandrel covered with a polymeric covering.

FIGS. 14A-14C illustrate a method of manufacturing the primary stent graft 310. FIG. 14A depicts a body forming mandrel 360 and a sleeve forming mandrel 370. The body forming mandrel 360 includes a slot or groove 361 configured to receive the sleeve forming mandrel 370. The body forming mandrel 360 is generally cylindrical in shape and formed from any suitable material, such as stainless steel, aluminum, etc. The sleeve forming mandrel 370 includes a convex shaped outer surface 371, wherein a curvature of the outer surface 371 corresponds with a curvature of an outer surface 362 of the body forming mandrel 360. The sleeve forming mandrel 370 further includes a convex shaped inner surface 372. A cross-section of the sleeve forming mandrel 370 includes an eye shape. The slot 361 includes a concave shape having a curvature to correspond to a curvature of the inner surface 372. In other embodiments, the slot 361 and the sleeve forming mandrel 370 can be of any suitable shape having a positive/negative mating relationship wherein the positive shape fits into the negative shape. A handle 375 may extend at an angle from a distal end of the sleeve forming mandrel 370.

As depicted in FIG. 14B, a polymeric covering 374 surrounds the sleeve forming mandrel 370. The covering 374 will be the wall 336 of the sleeve 330 of the primary stent graft 310, as previously described. The material of the wall 336 is previously described. The covering 374 can be applied using any suitable technique. For example, the covering 374 can be applied by wrapping strips of material around the mandrel, serially depositing material onto the mandrel, dipping the mandrel into a solvent based polymer solution, or spraying the mandrel with a solvent based polymer solution. Other application techniques are contemplated. As the arrows of FIG. 14B indicate, the covered sleeve forming mandrel 370 is disposed within the slot 361.

Figure 15:
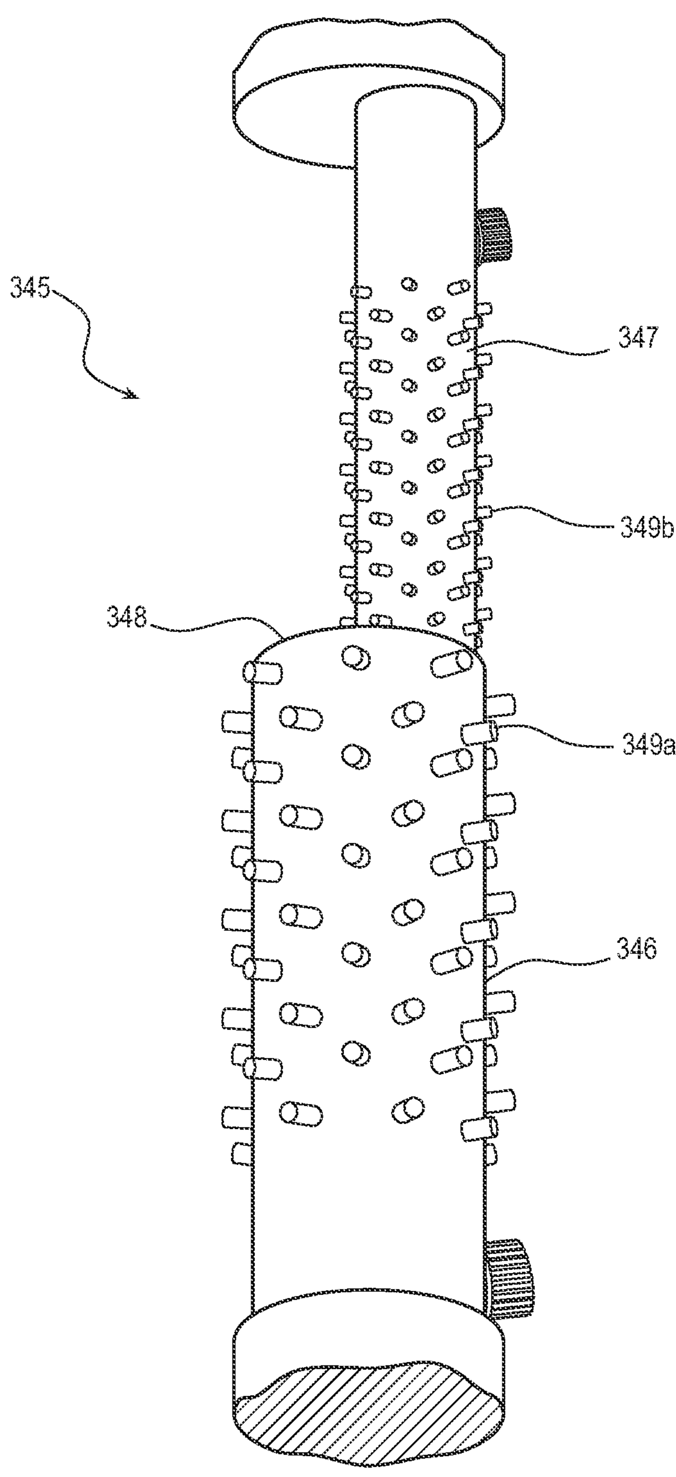
FIG. 15 is a perspective view of a wire stent winding mandrel.

As shown in FIG. 14C, a polymeric covering 363 is disposed around the body forming mandrel 360 and the covered sleeve forming mandrel 370 that has been disposed in slot 361. The covering 363 is configured to be the wall 323 of the body 311 of the primary stent graft 310 as previously described. The covering 363 can be applied using any suitable technique. For example, the covering 363 can be applied by wrapping strips of material around the mandrel, serially depositing material onto the mandrel, dipping the mandrel into a solvent based polymer solution, or spraying the mandrel with a solvent based polymer solution. Other application techniques are contemplated The wire stent 340 may be formed over a wire stent mandrel 345. As illustrated in FIG. 15, the wire stent mandrel 345 includes a proximal portion 346, a distal portion 347, and a square transition 348 disposed between the proximal and distal portions 346, 347. The pins 349*a*, 349*b* can be disposed in a pattern to form the shape of the wire stent 340 as previously described. A diameter of the pins 349*a* and 349*b* may be the same or different. The diameter of pins may range from about 0.38 millimeter to about 3.2 millimeters and may include any size suitable for creating a bend in the stent wire that is conducive for manufacture and durability of the finished stent graft device. The diameter of the pins 349*a*, 349*b* can determine a radius of a bend of the wire of the wire stent 340 as the wire is wound around the wire stent mandrel 345. For example, a radius of a bend of the wire around the pins 349*a* may be larger than a radius of a bend of the wire around the pins 349*b* thereby inducing different rates of outward force between proximal and distal portions 346, 347.

The formed wire stent 340 may be disposed over the body 311. An outer polymeric covering may be disposed over the wire stent 340. The covered wire stent 340 and body 311 may be sintered at about 385 degrees Centigrade to bind the outer covering, the wire stent 340, and the body 311 together. The body forming and sleeve forming mandrels 360, 370 can be removed from the primary stent graft 310.

Figure 16B:
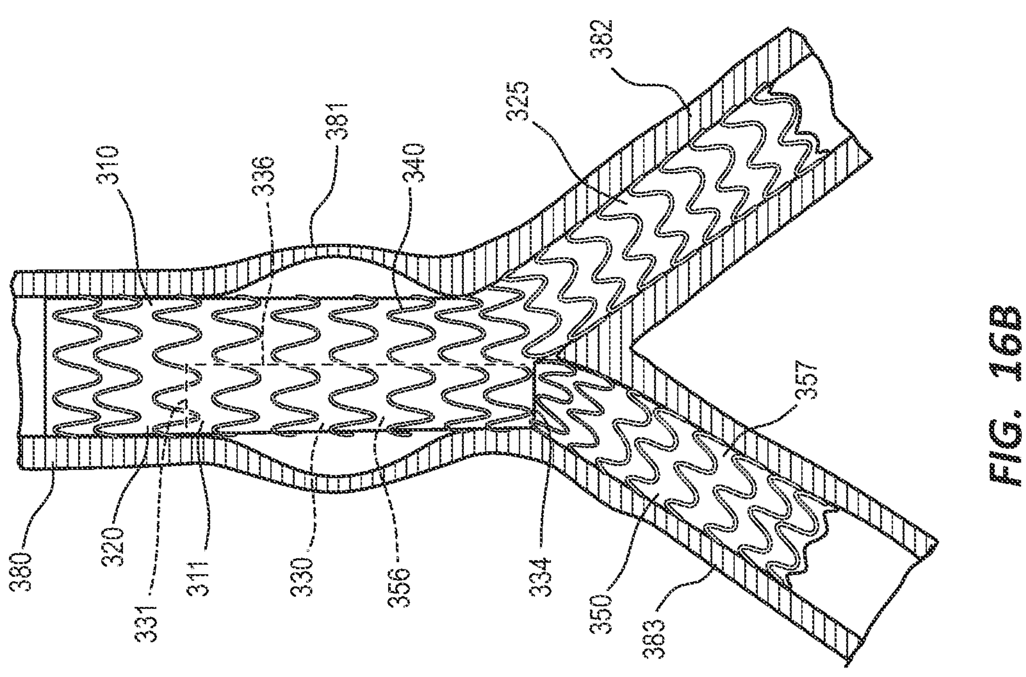
FIG. 16B is a side view of the bifurcated endovascular prosthesis of FIG. 11 disposed within the diseased aorta.
Figure 16A:
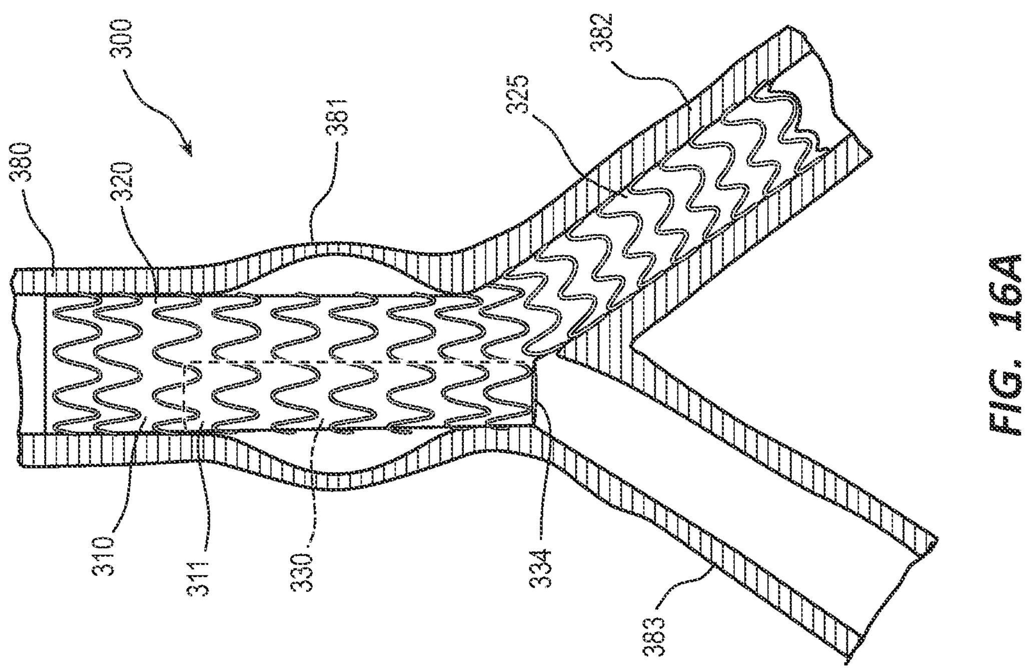
FIG. 16A is a side view of the primary stent graft of FIG. 12A disposed within a diseased aorta.

FIGS. 16A and 16B illustrate a method of implanting the bifurcated endovascular prosthesis 300 in a diseased blood vessel (e.g., aorta) and iliac arteries. FIG. 16A shows the primary stent graft 310 of the bifurcated endovascular prosthesis 300 deployed in the aorta 380. The primary stent graft 310 may be deployed using a delivery catheter system, wherein the primary stent graft 310 is radially compressed or crimped and disposed within the delivery catheter system. In various embodiments, the primary stent graft 310 may be deployed in any diseased arterial or venous vessel having a bifurcation, such as a coronary artery, a carotid artery, a popliteal artery, a common femoral artery, etc. When deployed, the body 311 may be radially expanded (e.g., self-expanded or balloon expanded) to compress the proximal portion 320 against a healthy tissue section of a wall of the aorta 380 proximal to a diseased section 381 of the aorta 380 such that the bifurcated endovascular prosthesis 300 may be secured in place. The diseased section 381 may be an aneurysm, a pseudoaneurysm, an aortic dissection, or any other type of vascular disease. The distal portion 325 may extend distally into a first iliac artery 382 and may be radially expanded to compress against a wall of the first iliac artery 382.

FIG. 16B shows the secondary stent graft 350 deployed and coupled to the primary stent graft 310. The secondary stent graft 350 may be deployed using a delivery catheter system, wherein the secondary stent graft 350 is radially compressed or crimped and disposed within the delivery catheter system. The catheter delivery system may be disposed into the sleeve 330 through the distal opening 334 and may be configured to open the closed proximal end 331 of the sleeve 330. The proximal portion 356 is deployed within the sleeve 330 and a distal portion 357 extends through the distal opening 334 and into the second iliac artery 383. The secondary stent graft 350 may be radially expanded (e.g., self-expanded or balloon expanded) to compress the proximal portion 356 against the wall 336 of the sleeve 330 and the distal portion 357 against a wall of the second iliac artery 383 to form a fluid tight seal and to secure the secondary stent graft 350 in place. When the bifurcated endovascular prosthesis 300 is fully deployed, as shown in FIG. 16B, blood can flow from the aorta 380; into the primary stent graft 310; and within the primary stent graft 310 the blood flow can be divided into two flows, a first flow continues through the primary stent graft 310 and exits into the first iliac artery 382, and the second flow enters the secondary stent graft 350, flows through the secondary stent graft 350, and exits into the second iliac artery 383. The blood flow rates into the first and second iliac arteries 382, 383 can be substantially equivalent.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of repairing a bifurcated blood vessel may include one or more of the following steps: deploying a primary stent graft of a bifurcated endovascular prosthesis in the bifurcated blood vessel, wherein a proximal portion of the primary stent graft is deployed adjacent a diseased portion of the bifurcated blood vessel and a distal portion of the primary stent graft is deployed in a first branch vessel; and deploying a secondary stent graft of the bifurcated endovascular prosthesis, wherein a proximal portion of the secondary stent graft is disposed within a pocket of the primary stent graft and a distal portion of the secondary stent graft is disposed within a second branch vessel. Other steps are also contemplated.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of an implanted medical device means the end of the device furthest from the heart. The proximal end refers to the opposite end, or the end nearest the heart. As specifically applied to a bifurcated endovascular prosthesis, the proximal end of the prosthesis refers to the end configured for deployment nearest the heart (along the blood flow path of the vasculature) and the distal end refers to the opposite end, the end farthest from the heart. If at one or more points in a procedure a physician changes the orientation of the prosthesis, as used herein, the term "proximal end" always refers to the end configured for deployment closest to the heart when implanted.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

The terms "a" and "an" can be described as one, but not limited to one. For example, although the disclosure may recite a body having "a pocket," the disclosure also contemplates that the body can have two or more pockets.

Unless otherwise stated, all ranges include both endpoints and all numbers between the endpoints.

Recitation in the claims of the term "first" with respect to a feature or element does not necessarily imply the existence of a second or additional such feature or element.

Various features are sometimes grouped together in a single embodiment, figure, or description thereof for the purpose of streamlining the disclosure. Many of these features may be used alone and/or in combination with one another. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A method of manufacturing a bifurcated endovascular prosthesis, comprising:

constructing a primary stent graft construct, comprising:

obtaining a pocket mandrel and a first body mandrel;

covering the pocket mandrel with a first polymeric covering;

disposing the covered pocket mandrel within a groove of the first body mandrel;

covering the covered pocket mandrel and the first body mandrel with a second polymeric covering; and constructing a secondary stent graft construct, comprising:

obtaining a second body mandrel; and covering the second body mandrel with a third polymeric covering.

2. The method of claim 1, wherein constructing the primary stent graft construct further comprises forming an opening in the first polymeric covering and the second polymeric covering adjacent a distal end of the pocket mandrel.

3. The method of claim 2, wherein constructing the primary stent graft further comprises:

winding a first wire around a plurality of winding pins of a primary wire stent mandrel to form a primary wire stent, wherein an area of the primary wire stent is void of the first wire;

disposing the primary wire stent over the covered pocket and body mandrels, wherein an area void of the first wire is disposed adjacent the opening; and covering the primary wire stent with a fourth polymeric covering.

4. The method of claim 3, wherein constructing the primary stent graft construct further comprises sintering the primary stent graft.

5. The method of claim 1, wherein construction of the secondary stent graft further comprises:

winding a second wire around a plurality of winding pins of a secondary wire stent mandrel to form a secondary wire stent;

disposing the secondary wire stent over the covered second body mandrel; and covering the secondary wire stent with a fifth polymeric covering.

6. The method of claim 5, wherein constructing the secondary stent graft construct further comprises sintering the secondary stent graft.

7. The method of claim 1, wherein covering the pocket mandrel with the first polymeric covering includes any one of wrapping strips of material around the pocket mandrel, serially depositing material onto the pocket mandrel, dipping the pocket mandrel into a solvent based polymer solution, and spraying the pocket mandrel with a solvent based polymer solution.

8. The method of claim 1, wherein covering the covered pocket mandrel and the body mandrel with the second polymeric covering includes any one of wrapping strips of material around the pocket mandrel, serially depositing material onto the pocket mandrel, dipping the pocket mandrel into a solvent based polymer solution, and spraying the pocket mandrel with the solvent based polymer solution.

9. The method of claim 1, wherein covering the second body mandrel with the third polymeric covering includes any one of wrapping strips of material around the pocket mandrel, serially depositing material onto the pocket mandrel, dipping the pocket mandrel into a solvent based polymer solution, and spraying the pocket mandrel with a solvent based polymer solution.

10. The method of claim 3, wherein covering the primary stent with the fourth polymeric covering includes any one of wrapping strips of material around the pocket mandrel, serially depositing material onto the pocket mandrel, dipping the pocket mandrel into a solvent based polymer solution, and spraying the pocket mandrel with a solvent based polymer solution.

11. The method of claim 5, wherein covering the secondary stent with the fifth polymeric covering includes any one of wrapping strips of material around the pocket mandrel, serially depositing material onto the pocket mandrel, dipping the pocket mandrel into a solvent based polymer solution, and spraying the pocket mandrel with a solvent based polymer solution.

12. The method of claim 1, wherein a distal end of the pocket mandrel comprises a surface having an angle ranging from 30 degrees to 90 degrees relative to a longitudinal axis of the pocket mandrel.

13. A method of manufacturing a primary stent graft of a bifurcated endovascular prosthesis comprising constructing a primary stent graft construct, comprising:

obtaining a pocket mandrel and a body mandrel;

covering the pocket mandrel with a first polymeric covering;

disposing the covered pocket mandrel within a groove of the body mandrel;

covering the covered pocket mandrel and the body mandrel with a second polymeric covering; and forming an opening in the first polymeric covering and the second polymeric covering adjacent a distal end of the pocket mandrel.

14. The method of claim 13, wherein constructing the primary stent graft further comprises:

winding a wire around a plurality of winding pins of a primary wire stent mandrel to form a primary wire stent, wherein an area the primary wire stent is void of the wire;

disposing the primary wire stent over the covered pocket and body mandrels, wherein the area void of the wire is disposed adjacent the opening; and covering the primary wire stent with a third polymeric covering.

15. The method of claim 14, wherein constructing the primary stent graft construct further comprises sintering the primary stent graft construct at 385 degrees C.

16. The method of claim 13, wherein covering the pocket mandrel with the first polymeric covering includes any one of wrapping strips of material around the pocket mandrel, serially depositing material onto the pocket mandrel, dipping the pocket mandrel into a solvent based polymer solution, and spraying the pocket mandrel with a solvent based polymer solution.

17. The method of claim 13, wherein covering the covered pocket mandrel and the body mandrel with the second polymeric covering includes any one of wrapping strips of material around the pocket mandrel, serially depositing material onto the pocket mandrel, dipping the pocket mandrel into a solvent based polymer solution, and spraying the pocket mandrel with a solvent based polymer solution.

18. The method of claim 14, wherein covering the primary stent with the third polymeric covering includes any one of wrapping strips of material around the pocket mandrel, serially depositing material onto the pocket mandrel, dipping the pocket mandrel into a solvent based polymer solution, and spraying the pocket mandrel with a solvent based polymer solution.

19. The method of claim 13, wherein the pocket mandrel comprises any one of a circular cross-sectional shape, an elliptical cross-sectional shape, and a cross-sectional D-shape.

* * * * *